United States Patent
Jakob et al.

(10) Patent No.: US 10,493,214 B2
(45) Date of Patent: Dec. 3, 2019

(54) MEDICAL INJECTION DEVICE

(71) Applicant: Raumedic AG, Helmbrechts (DE)

(72) Inventors: Thomas Jakob, Selb (DE); Sebastian Maag, Bayreuth (DE); Tobias Festel, Sparneck (DE); Thomas Braun, Hof (DE); Frank Skaper, Leupoldsgrün (DE)

(73) Assignee: Raumedic AG, Münchberg (DE)

(*) Notice: Subject to any disclaimer, the term of this patent is extended or adjusted under 35 U.S.C. 154(b) by 926 days.

(21) Appl. No.: 14/339,812

(22) Filed: Jul. 24, 2014

(65) Prior Publication Data

US 2015/0032061 A1  Jan. 29, 2015

(30) Foreign Application Priority Data

Jul. 24, 2013 (DE) .................. 10 2013 214 429

(51) Int. Cl.
*A61M 5/32* (2006.01)

(52) U.S. Cl.
CPC .......... *A61M 5/326* (2013.01); *A61M 5/3243* (2013.01); *A61M 5/3245* (2013.01); *A61M 5/3271* (2013.01); *A61M 5/3202* (2013.01); *A61M 2005/325* (2013.01); *A61M 2005/3247* (2013.01)

(58) Field of Classification Search
CPC .............. A61M 5/3243; A61M 5/3245; A61M 5/3257; A61M 5/326; A61M 5/3271; A61M 2005/3247
See application file for complete search history.

(56) References Cited

U.S. PATENT DOCUMENTS

| 4,573,976 | A | * | 3/1986 | Sampson | A61M 5/3269 604/198 |
| 4,795,432 | A | * | 1/1989 | Karczmer | A61M 5/3257 604/110 |
| 4,813,940 | A | * | 3/1989 | Parry | A61M 5/283 604/198 |
| 4,838,871 | A | | 6/1989 | Luther | |
| 4,892,521 | A | * | 1/1990 | Laico | A61M 5/3243 604/192 |
| 4,897,083 | A | * | 1/1990 | Martell | A61M 5/3202 604/192 |

(Continued)

FOREIGN PATENT DOCUMENTS

| CH | 685979 | 11/1995 |
| DE | 695 02 357 | 1/1999 |

(Continued)

*Primary Examiner* — Kami A Bosworth
(74) *Attorney, Agent, or Firm* — Boyle Fredrickson S.C.

(57) ABSTRACT

A medical injection device has a syringe. The syringe has a container for the medium to be injected and an injection cannula, which communicates with the container. A needle guard of the injection device can be moved between an injection position and a safe position. In the injection position, the injection cannula can be uncovered in order to inject the medium. In the safe position, a cannula tip of the injection cannula is recessed in a protective component of the needle guard. A securing device securely fixes the protective component in the safe position. The result is an injection device having a needle guard that can be manipulated intuitively and operated safely.

11 Claims, 21 Drawing Sheets

(56) References Cited

U.S. PATENT DOCUMENTS

| | | | |
|---|---|---|---|
| 4,923,447 A | 5/1990 | Morgan | |
| 4,927,416 A * | 5/1990 | Tomkiel | A61M 5/315 604/198 |
| 4,944,397 A | 7/1990 | Miller | |
| 4,982,842 A | 1/1991 | Hollister | |
| 5,067,945 A * | 11/1991 | Ryan | A61M 5/3243 600/576 |
| 5,139,489 A | 8/1992 | Hollister | |
| 5,154,285 A | 10/1992 | Hollister | |
| 5,232,454 A | 8/1993 | Hollister | |
| 5,232,455 A | 8/1993 | Hollister | |
| 5,242,416 A * | 9/1993 | Hutson | A61M 5/3216 604/192 |
| 5,277,311 A | 1/1994 | Hollister | |
| 5,295,965 A * | 3/1994 | Wilmot | A61M 5/2033 604/136 |
| 5,312,367 A | 5/1994 | Nathan | |
| 5,342,322 A | 8/1994 | Nathan et al. | |
| 5,423,765 A | 6/1995 | Hollister | |
| 5,498,243 A * | 3/1996 | Vallelunga | A61M 5/3243 604/187 |
| 5,584,816 A | 12/1996 | Gyure et al. | |
| 5,595,566 A * | 1/1997 | Vallelunga | A61M 5/3243 604/110 |
| 5,632,732 A | 5/1997 | Szabo et al. | |
| 5,643,219 A | 7/1997 | Burns | |
| 5,681,291 A * | 10/1997 | Galli | A61M 5/2033 604/156 |
| 6,036,675 A * | 3/2000 | Thorne | A61M 5/24 128/919 |
| 7,850,661 B2 * | 12/2010 | Chevallier | A61M 5/326 604/110 |
| 2004/0010234 A1 * | 1/2004 | Hung | A61M 5/3243 604/198 |
| 2005/0107748 A1 * | 5/2005 | Thorne | A61M 5/158 604/263 |
| 2008/0177235 A1 * | 7/2008 | DiBiasi | A61M 5/326 604/192 |
| 2008/0177237 A1 * | 7/2008 | Stonehouse | A61M 5/326 604/263 |
| 2009/0259193 A1 * | 10/2009 | Chen | A61M 5/3243 604/192 |
| 2014/0039407 A1 * | 2/2014 | Schoonmaker | A61M 5/3202 604/198 |
| 2014/0243755 A1 * | 8/2014 | Slemmen | A61M 5/3202 604/198 |
| 2014/0257200 A1 * | 9/2014 | Auerbach | A61B 17/3496 604/263 |

FOREIGN PATENT DOCUMENTS

| | | |
|---|---|---|
| EP | 0 272 035 A2 | 6/1988 |
| EP | 0 460 914 | 11/1995 |
| EP | 0 692 271 | 4/2002 |
| EP | 0 707 860 | 12/2002 |
| EP | 0 885 621 | 12/2002 |
| EP | 0 862 920 | 1/2003 |
| EP | 1 568 321 | 8/2005 |
| EP | 1 587 419 | 11/2009 |
| EP | 1 592 346 | 7/2011 |
| EP | 1 525 016 | 11/2011 |
| EP | 2 578 255 A1 | 4/2013 |
| EP | 2 578 256 A1 | 4/2013 |
| WO | 91/09639 | 7/1991 |
| WO | 2014/048298 A1 | 4/2014 |

* cited by examiner

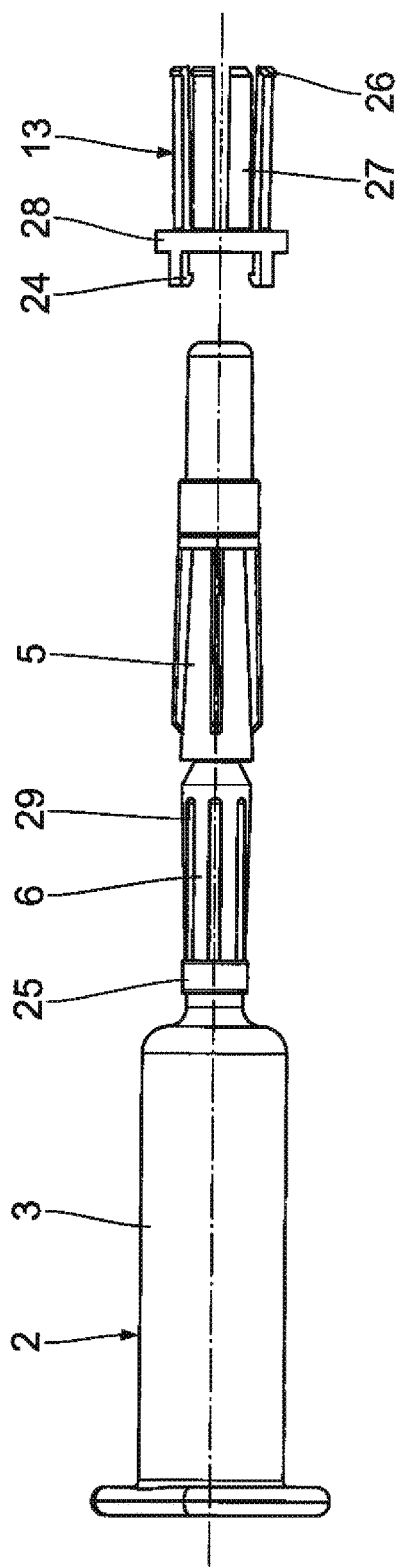
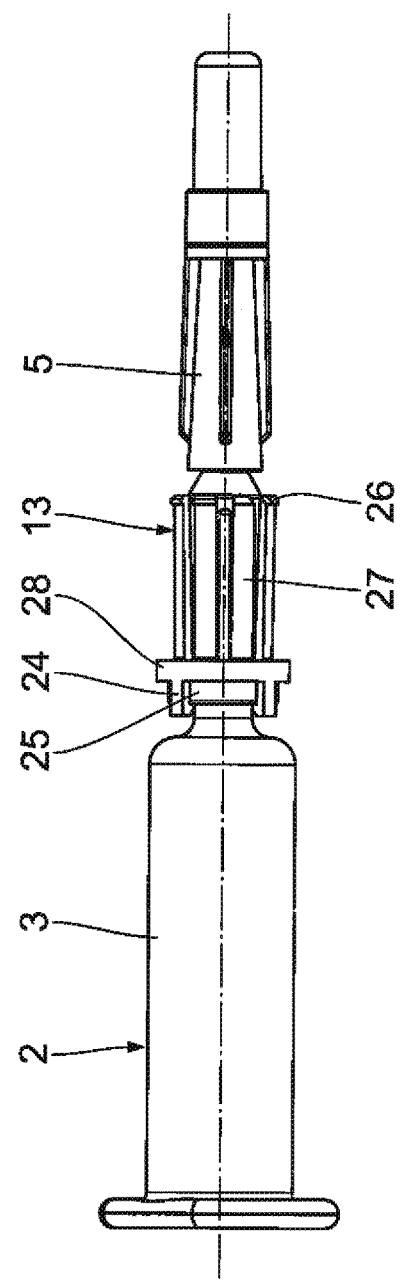
Fig. 8
Fig. 9

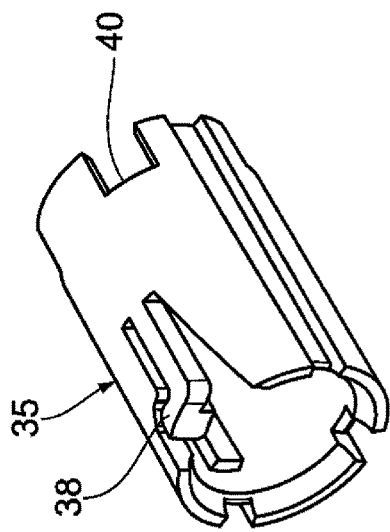
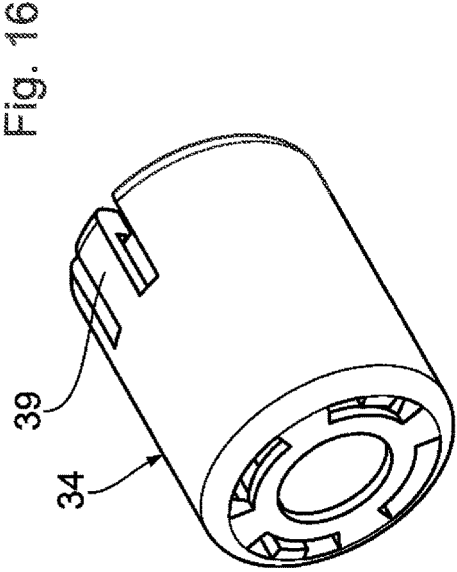
Fig. 15
Fig. 16
Fig. 17

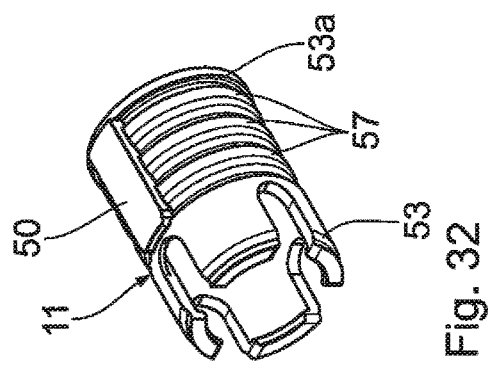
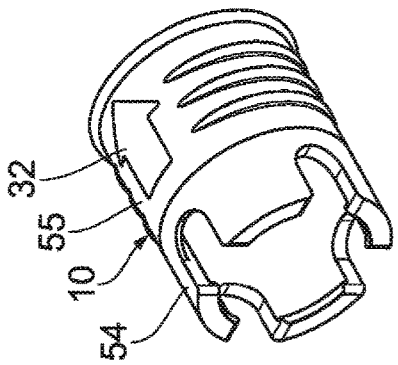
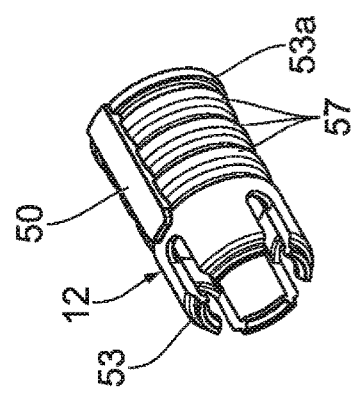

MEDICAL INJECTION DEVICE

CROSS-REFERENCE TO RELATED APPLICATIONS

This application claims the priority of German patent application, Serial No. DE 10 2013 214 429.6, filed Jul. 24, 2013, pursuant to 35 U.S.C. 119(a)-(d), the content of which is incorporated herein by reference in its entirety as if fully set forth herein.

FIELD OF THE INVENTION

The invention relates to a medical injection device comprising a syringe and a needle guard.

BACKGROUND OF THE INVENTION

Medical injection devices with needle guards are known from EP 460 914 B1; EP 707 860 B1; U.S. Pat. No. 4,838,871; EP 692 271 B1; U.S. Pat. Nos. 4,944,397; 4,982,842; 5,232,455; 5,139,489; 5,154,285; 5,277,311; 5,232,454; 5,312,367; 5,342,322; 5,423,765; 5,643,219; WO 1991/009639 A2; EP 862 920 B1; EP 885 621 B1; EP 1 525 016 B1; EP 1 568 321 A1; EP 1 587 419 B1; EP 1 592 346 B1; U.S. Pat. Nos. 5,584,816; 5,632,732; CH 685 979 A5 and DE 695 02 357 T2.

SUMMARY OF THE INVENTION

The object of the present invention is to develop an injection device of the type described in the introductory part such that a needle guard that can be manipulated intuitively and operated safely is produced.

This object is attained according to the invention by a medical injection device comprising a needle guard and a securing device having the features specified in claim 1.

The securing device holds the protective component securely in the safe position as soon as the protective component reaches the safe position. The securing device can be designed as a locking securing device, for example as an axially and/or radially locking securing device. Alternatively or additionally, the securing device can securely fix the protective component in the safe position by means of an interlocking connection, for example, by means of a slide catch design or bayonet joint. The needle guard can be actively movable from the injection position to the safe position, and can be designed to be moved by the user. The needle guard as a whole and the securing device can comprise plastic components.

A guard locking assembly according to claim 2 results in a particularly secure fixation of the protective component in the safe position. The guard locking assembly can be designed such that once the protective component has been moved to the safe position, the user can no longer move said component out of the safe position without destroying it.

An injection connecting assembly according to claim 3 prevents the needle guard from being unintentionally moved from the injection position to the safe position. The injection connecting assembly can be designed as locking, for example as axially and/or radially locking, and/or as an interlocking connection, for example, as a slide catch or bayonet joint, as described above in connection with the guard locking assembly.

An injection locking assembly according to claim 4 can be implemented at a low production cost. The injection locking assembly can be designed to be overcome, for example, by the user releasing locking components by applying a specific amount of pressure to the needle guard.

An embodiment involving a telescoping needle guard according to claim 5 can be compact in design. In the injection position, the telescoping sleeves can be arranged one on top of the other. In the safe position, the telescoping sleeves can be arranged in the extended position. The injection cannula can be encompassed on all sides by the protective telescoping sleeve. The telescoping sleeves can be connected to one another by an interlocking and/or locking assembly. At least one of the telescoping sleeves, which is arranged in another of the telescoping sleeves, can have a conical outer wall. This will ensure a uniform application of force as the interlocking and/or locking assembly is being moved between the injection position and the safe position. This can improve the intuitive manipulation of the needle guard during the move from the injection position to the safe position. Between a locked position that establishes the injection position between the telescoping components and a locked position that establishes the safe position of the telescoping components, at least one intermediate locked position can be established by corresponding locked intermediate stages. The locked intermediate stages can particularly be implemented by means of peripheral grooves in outer walls of each of the inner telescoping sleeves. The locking assembly can be designed as a radially and/or axially acting locking connection. The directional indicators "radial" and "axial" refer in this case to the direction of movement of locking components in relation to a central longitudinal axis of the needle guard during movement between a locked position and a released position.

At least one additional telescoping sleeve according to claim 6 enables a greater travel distance of the telescoping needle guard between the safe position and the injection position, therefore allowing longer injection cannula to be covered with a compact overall axial length. Precisely one additional telescoping sleeve may be arranged between the connecting telescoping sleeve and the protective telescoping sleeve. A plurality of such additional telescoping sleeves, for example two or three additional telescoping sleeves, may also be provided in a telescoping needle guard of this type.

A guard locking assembly according to claim 7 can have locking teeth that have a preferred direction, ensuring a one-way movement of the protective component of the needle guard to the safe position, and/or ensuring a defined end position of the protective component in the safe position. The guard locking assembly can have a plurality of rows of locking teeth arranged around the telescoping sleeves in the circumferential direction, with each said row interacting with an opposing locking element. The locking teeth can be formed on and integrally with the respective telescoping sleeve.

At least one tongue/groove device according to claim 8 ensures a defined and secure guideway between the telescoping sleeves during the relative displacement of said sleeves between the injection position and the safe position.

An interlocking adapter according to claim 9 can be designed for adapting the needle guard to commercially designed syringes. The interlocking adapter can be connected by means of an interlocking and/or locking connection to both the syringe and the needle guard. The interlocking connection adapter can be prevented from rotating by both the syringe and the needle guard. The interlocking adapter can be designed as an adapter sleeve that can be attached axially or as a C-shaped adapter that can be snapped on radially. At the same time, the interlocking adapter can serve as a connecting sleeve in a telescoping embodiment of the needle guard. This connecting sleeve can be one of the telescoping sleeves.

A multicomponent injection-molded embodiment according to claim 10 expands the number of possible configurations of the components of the needle guard. The multicomponent injection-molded part can be embodied as a two-component injection-molded part or as an injection-molded part having more than two components, for example, three components, four components, five components or even more components. Softer plastics may be combined with harder plastics. For example, softer plastics may be used for a grip section of the needle guard or for molded components which are placed against opposing components to compensate for play and/or to create and/or increase frictional contact between the respective molded component and the respective opposing component.

A soft component of the multicomponent injection-molded part can be made of one or more thermoplastic elastomers (TPE), polyurethane or silicone, for example. A hard component of the multicomponent injection-molded part can be made of polypropylene, of polyethylene, of ABS (acrylonitrile-butadiene styrene), of a thermoplastic material based on methyl methacrylate, acrylonitrile, butadiene and styrene (MABS), of polyoxymethylene (POM), of polybutylene terephthalate (PBT) or of blended systems, that is, a mixture based on polyolefins and polyamide.

The specifications of claims 11 and 12 provide advantageous variants for the use of multicomponent injection-molded parts.

A multicomponent injection-molded design of the interlocking element and the interlocking element supporting piece allows the at least one interlocking element, which can be designed as an axial rib, to be made of a softer plastic material than that of the interlocking element supporting piece, thereby improving the frictional contact between the interlocking elements and the inner opening and connecting section. This improves the rotation prevention of the interlocking adapter relative to the opening and connecting section.

BRIEF DESCRIPTION OF THE DRAWINGS

In the following, embodiment examples of the invention will be specified in greater detail, in reference to the set of drawings. The drawings show:

FIGS. 8 to 11 momentary positions during the assembly of the injection device;

FIG. 15 an interlocking adapter, embodied as a C-shaped adapter that can be snapped on radially, for connecting the needle guard according to FIGS. 12 to 14 to the syringe in an interlocking manner;

FIG. 16 a telescoping sleeve of the needle guard according to FIGS. 12 to 14, arranged between the interlocking adapter according to FIG. 15 and a protective telescoping sleeve of the needle guard;

FIG. 17 the protective telescoping sleeve of the needle guard according to FIGS. 12 to 14;

FIGS. 27 to 35 illustrations similar to those of FIGS. 18 to 26 of components of a further embodiment of a needle guard for a syringe;

DETAILED DESCRIPTION OF AT LEAST ONE PREFERRED EMBODIMENT

Figure 1:
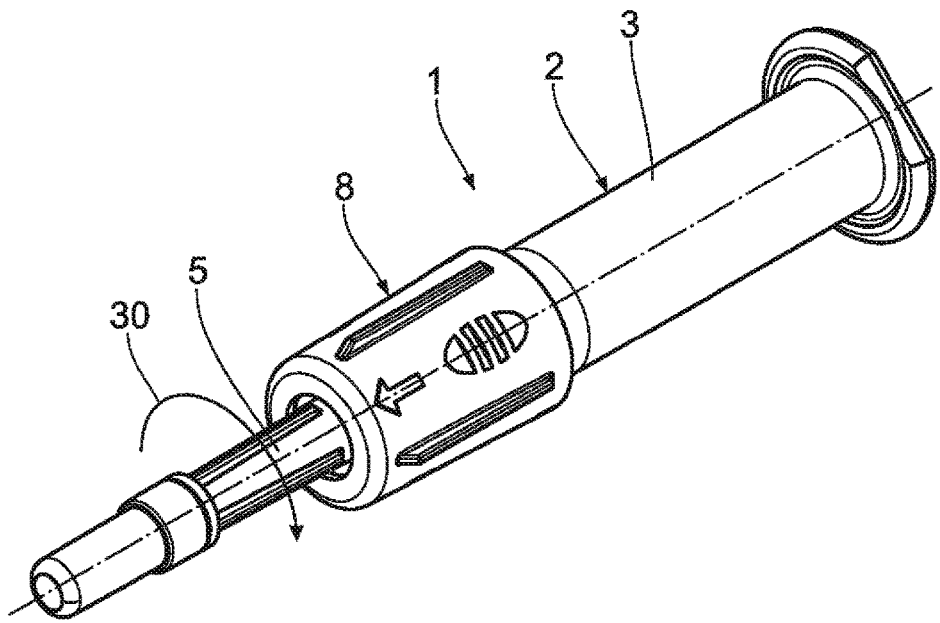
FIG. 1 A medical injection device comprising a syringe and a telescoping needle guard in the assembled state, ready for distribution.

FIGS. 1 to 11 show one embodiment of a medical injection device 1. The injection device 1 has a syringe 2. Said syringe comprises a container 3 for the medium to be injected. Container 3 can be embodied as a syringe container 3 designed to accommodate a syringe plunger, which is not shown in the drawing. Syringe 2 further comprises an injection cannula 4, which is clearly visible in FIG. 2 and is covered by an original safety cap 5 in FIG. 1. In the originally delivered state of the injection device 1, as shown in FIG. 1, the original safety cap 5 is placed on the injection cannula 4 and is locked axially to an end of container 3 on the cannula side. To inject the medium, injection cannula 4 communicates with container 3 via a cannula-side opening and connecting section 6 of container 3, which is visible in the sectional illustration of FIG. 5. Opening and connecting section 6 is pushed onto a conically tapered opening end of a glass element of container 3, and can be connected thereto in an interlocking manner, particularly locked thereto. Injection cannula 4, which is a metallic cannula, is connected to opening section 6 via a plug-in and/or conical connection 7. In a variant of the injection device 1 not shown here, conical connection 7 is designed as a luer-lock connection. An inner wall of opening section 6 can be latched or otherwise connected in an interlocking manner in the region of plug-in and/or conical connection 7 to an outer wall of a cannula attachment.

Apart from injection cannula 4, all the components of injection device 1 are made of plastic. In principle, injection cannula 4 can also be made of plastic.

Injection device 1 further comprises a needle guard 8. Said needle guard can be moved between an injection position, shown in FIG. 2, in which injection cannula 4 can be uncovered, for example for subcutaneous or intravenous injection of the medium, and a safe position, shown in FIG. 4, in which a cannula tip 9 of injection cannula 4 is recessed in a protective component 10 of needle guard 8.

Needle guard 8 encompasses opening section 6 in the form of a sleeve, and comprises at least two telescoping sleeves. In the embodiment according to FIGS. 1 to 11, needle guard 8 has a total of three telescoping sleeves 10, 11 and 12, with one of these three telescoping sleeves, protective telescoping sleeve 10, serving as the protective component of needle guard 8. Protective telescoping sleeve 10 is also the outermost of the three telescoping sleeves 10 to 12 of needle guard 8. An innermost of the three telescoping sleeves, connecting telescoping sleeve 12, is connected via an interlocking adapter 13 to syringe 2. Between innermost telescoping sleeve 12 and outermost telescoping sleeve 10 of needle guard 8, telescoping sleeve 11 is positioned as an additional telescoping sleeve of needle guard 8.

In the injection position, telescoping sleeves 10 to 12 are pushed completely one on top of the other. In the injection position, needle guard 8 covers the conical connection 7 axially, so that said connection is not accessible from the outside. In the safe position, telescoping sleeves 10 to 12 are extended relative to one another.

Figure 5:
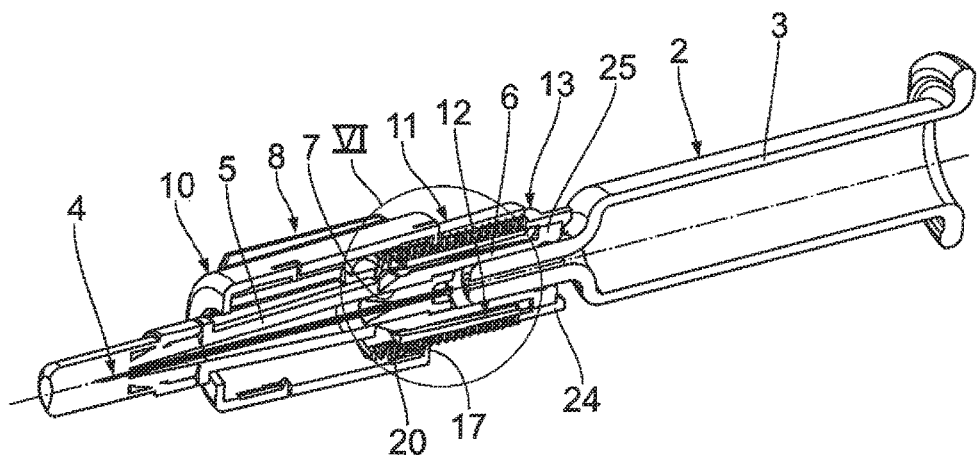
FIG. 5 a partial longitudinal cross-section of the injection device with the original safety cap attached, wherein the telescoping needle guard is shown in a position between the injection position and the safe position.
Figure 6:
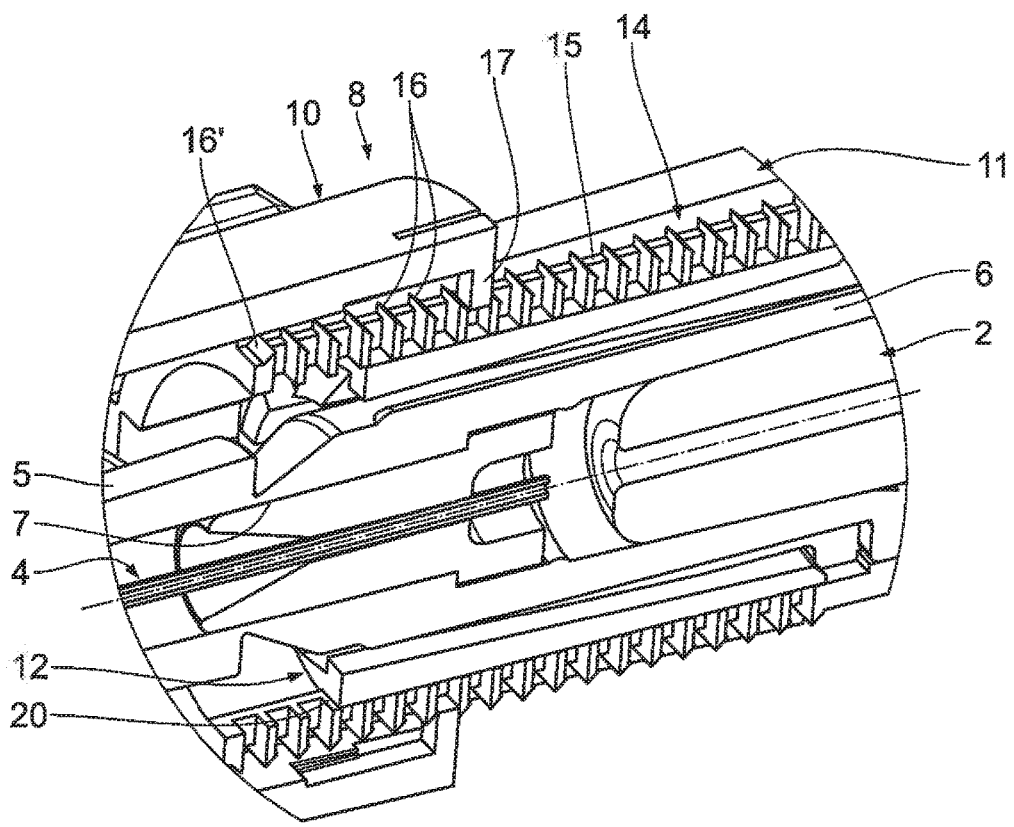
FIG. 6 an enlarged sectional illustration of detail VI in FIG. 5.

FIGS. 5 and 6 show details of the injection device 1 and particularly details of the needle guard 8.

A securing device in the form of a guard locking assembly 14 is provided for securely fixing the protective component, that is, the outermost protective telescoping sleeve 10, in the safe position. Said assembly comprises rows of locking teeth 15 comprising locking teeth 16 arranged in a row along center telescoping sleeve 11 and along inner connecting telescoping sleeve 12. Each of telescoping sleeves 11 and 12 has two outer rows of locking teeth 15 arranged in the circumferential direction around the longitudinal axis of the injection device, opposite one another. The two rows of locking teeth 15 of center telescoping sleeve 11 are offset by 90° in the circumferential direction around the longitudinal axis of injection device 1 relative to the two rows of teeth 15 of inner connecting telescoping sleeve 12.

An opposing locking element 17 of outer protective telescoping sleeve 10 and/or an opposing locking element 18 (cf. FIG. 7) of center telescoping sleeve 11 engages with locking teeth 16 in each case. The locking teeth 16 have a sawtooth profile in the axial longitudinal cross-section of the injection device, with a preferred direction to ensure the one-way movement of telescoping sleeves 10 and 11 from the injection position to the extended safe position. A locking tooth 16' (cf. FIG. 6), which corresponds to the maximum extended relative position of the associated telescoping sleeves 10, 11, has a precisely opposite preferred direction in the axial cross-section which defines the final extended position, that is, the safe position of needle guard 8.

The locking teeth 16 are formed on and integral with the respective telescoping sleeve 11, 12.

Tongue/groove guide devices 19 of needle guard 8 ensure a telescoping guideway while simultaneously preventing rotation between two of the three adjacent telescoping sleeves 10 to 12, that is, between telescoping sleeves 10 and 11 on one side and telescoping sleeves 11 and 12 on the other side.

Figure 7:
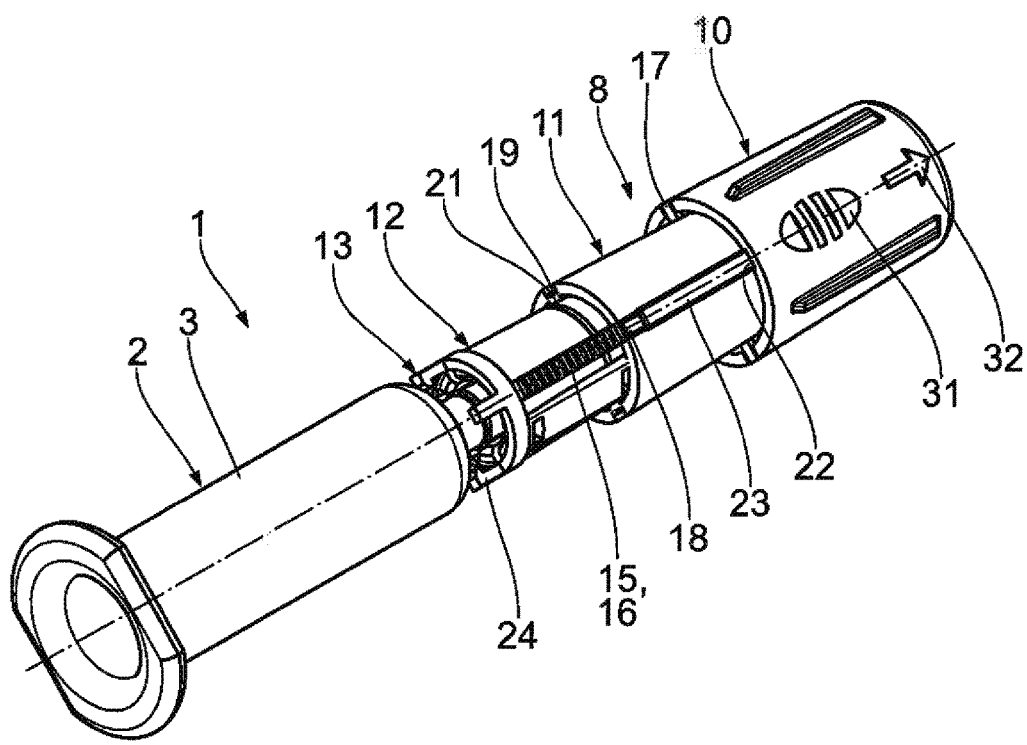
FIG. 7 an enlarged view of a section of the injection device in the safe position.
Figure 10:
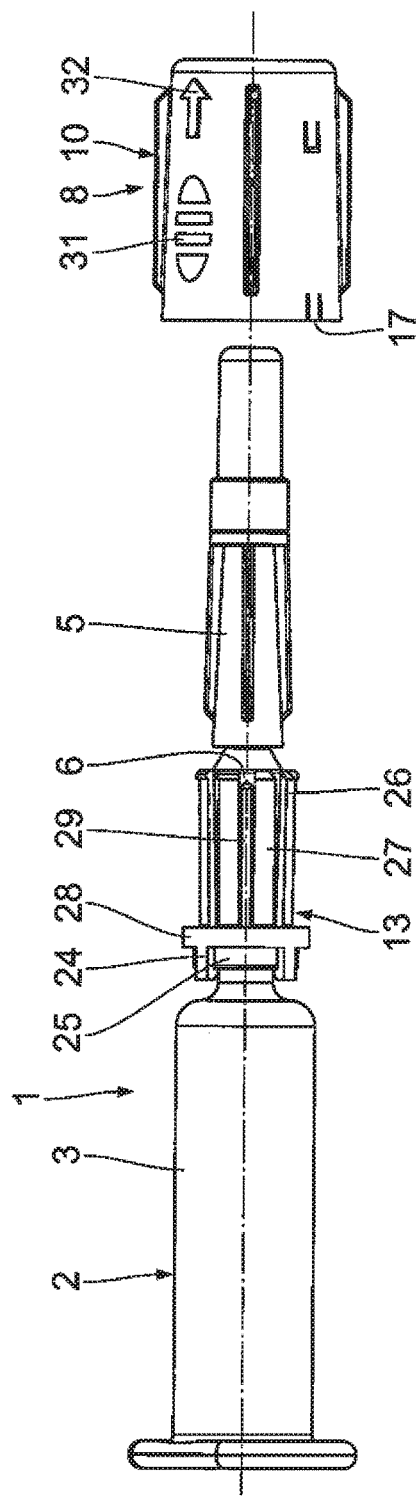

FIG. 7 shows a groove 20 in one of the tongue/groove guide devices 19, which is implemented as an axial longitudinal groove in an outer peripheral wall of inner connecting telescoping sleeve 12. A complementary tongue 21, which is designed as projecting inward on an inner wall of center telescoping sleeve 11, engages in this groove 20. Tongue 21 of center telescoping sleeve 11, which interacts with groove 20 of inner telescoping sleeve 12 as a guide, is formed by the inner ends of the remaining teeth 16 of center telescoping sleeve 11.

A further tongue/groove guide device 19 is formed by longitudinal axial grooves 22 in the inner peripheral wall of the outer protective telescoping sleeve 10 and by tongues 23, which are complementary to said grooves and are designed as projecting radially outward from the outer peripheral wall of center telescoping sleeve 11. In each case, two similar tongue/groove guide devices 19 are arranged opposite one another relative to the longitudinal axis of injection device 1. In each case, referred to one of telescoping sleeves 10 to 12, a locking component of guard locking assembly 14 alternates with a component of the tongue/groove guide device 19 in 90° steps in the circumferential direction around the longitudinal axis of injection device 1.

FIGS. 8 to 11 show momentary positions during the assembly of injection device 1. Interlocking adapter 13 is locked onto container 3 of syringe 2 by means of latching hooks 24. For this purpose the latching hooks 24 engage behind a locking collar 25 of container 3, which is located at the transition to opening section 6.

Inner connecting telescoping sleeve 12 is connected axially to interlocking adapter 13 via a plurality of latching elements 26, which are formed on unattached ends of locking tongues 27 of interlocking adapter 13. The locking tongues 27 extend in an axial direction and are formed on a common ring support 28 of interlocking adapter 13. As a whole, this gives interlocking adapter 13 the form of an adapter sleeve that can be attached axially. The distance between two locking tongues 27 that are adjacent in the circumferential direction around the longitudinal axis of injection device 1, and the number of said locking tongues 27 match the width and the number of axially extending peripheral ribs 29 that are formed on the outside of opening section 6 of container 3. When interlocking adapter 13 is attached, each locking tongue 27 is inserted between two adjacent peripheral ribs 29, thereby preventing interlocking adapter 13 from rotating relative to container 3, more specifically, relative to opening and connecting section 6 of container 3. An inner wall of inner connecting telescoping sleeve 12 is provided with axial structures, which are not illustrated in greater detail in the drawing, and which, when inner connecting telescoping sleeve 12 is snapped onto interlocking adapter 13, prevent inner connecting telescoping sleeve 12 from rotating relative to interlocking adapter 13. The inner axial structures of connecting telescoping sleeve 12 engage between adjacent locking tongues 27 of interlocking adapter 13.

When inner connecting telescoping sleeve 12 is snapped on, latching elements 26 engage behind a complementary locking collar of connecting telescoping sleeve 12, which is not illustrated in greater detail in the drawing.

An injection connecting assembly, designed as an injection locking assembly, serves to fix protective telescoping sleeve 10, that is, the protective component of needle guard 8, on the syringe 2 in the injection position in an interlocking connection. The locking components of this injection locking assembly are the outer edges of the unattached ends of the latching hooks 24 of interlocking adapter 13 on one side, and the opposite locking elements 17 of protective telescoping sleeve 10 that engage behind said outer edges in the injection position on the other side. This injection locking assembly 17, 24 can be overcome by releasing the opposing locking elements 17 from their engagement behind the latching tongues 24. This can be achieved by applying a defined amount of pressure to needle guard 8.

The injection device 1 is assembled as follows: To begin with, the syringe 2 is provided in its commercially distributed form, which is shown in FIG. 8. Needle guard 8 comprising sleeves 10 to 12 is preassembled in the injection position, in which the telescoping sleeves are pushed one completely on top of the other. Interlocking adapter 13 is then pushed onto the syringe 2 from the cannula side of the syringe 2, guided by latching hooks 24, until the latching hooks 24 engage with and lock behind locking collar 25 of container 3 (cf. FIG. 9). The preassembled needle guard 8 with the three telescoping sleeves 10 to 12 inserted one into the other and locked to one another is then pushed onto syringe 2, likewise from the cannula side, until inner connecting telescoping sleeve 12 has locked onto interlocking adapter 13, with the locking tongues 27 pressed radially between the peripheral ribs 29 to prevent rotation, and until the injection locking assembly 17, 24 is locked together. Inner connecting telescoping sleeve 12 is pushed onto interlocking adapter 13, oriented in the circumferential direction such that the inner axial structures of connecting telescoping sleeve 12 engage between locking tongues 27 of interlocking adapter 13. When inner connecting telescoping sleeve 12 is pushed all the way on, a guiding stop collar of connecting telescoping sleeve 12 comes to rest at a facing end wall of ring support 28 of interlocking adapter 13.

At the same time, inner structures of connecting telescoping sleeve 12 serve as means for holding the locking tongues 27 down between the peripheral ribs 29 of opening section 6 of syringe 2.

Figure 11:
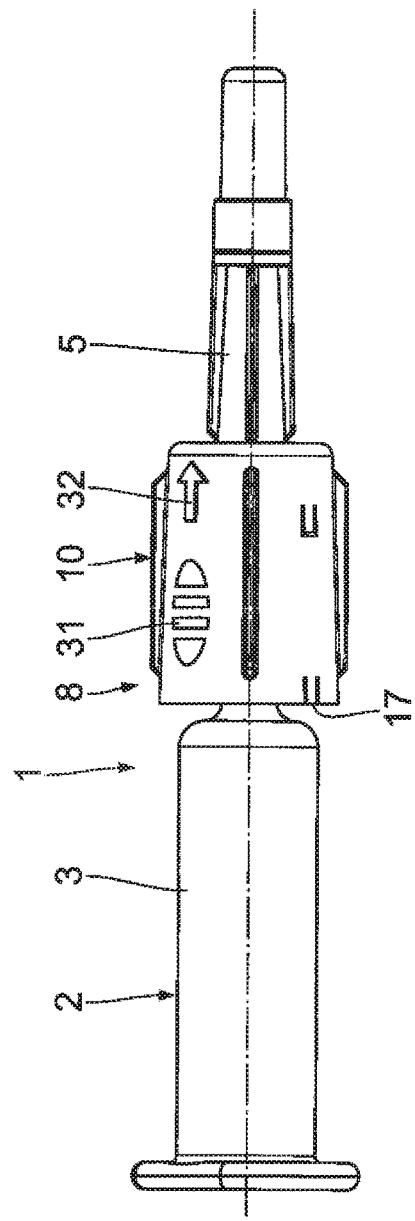
Figure 12:
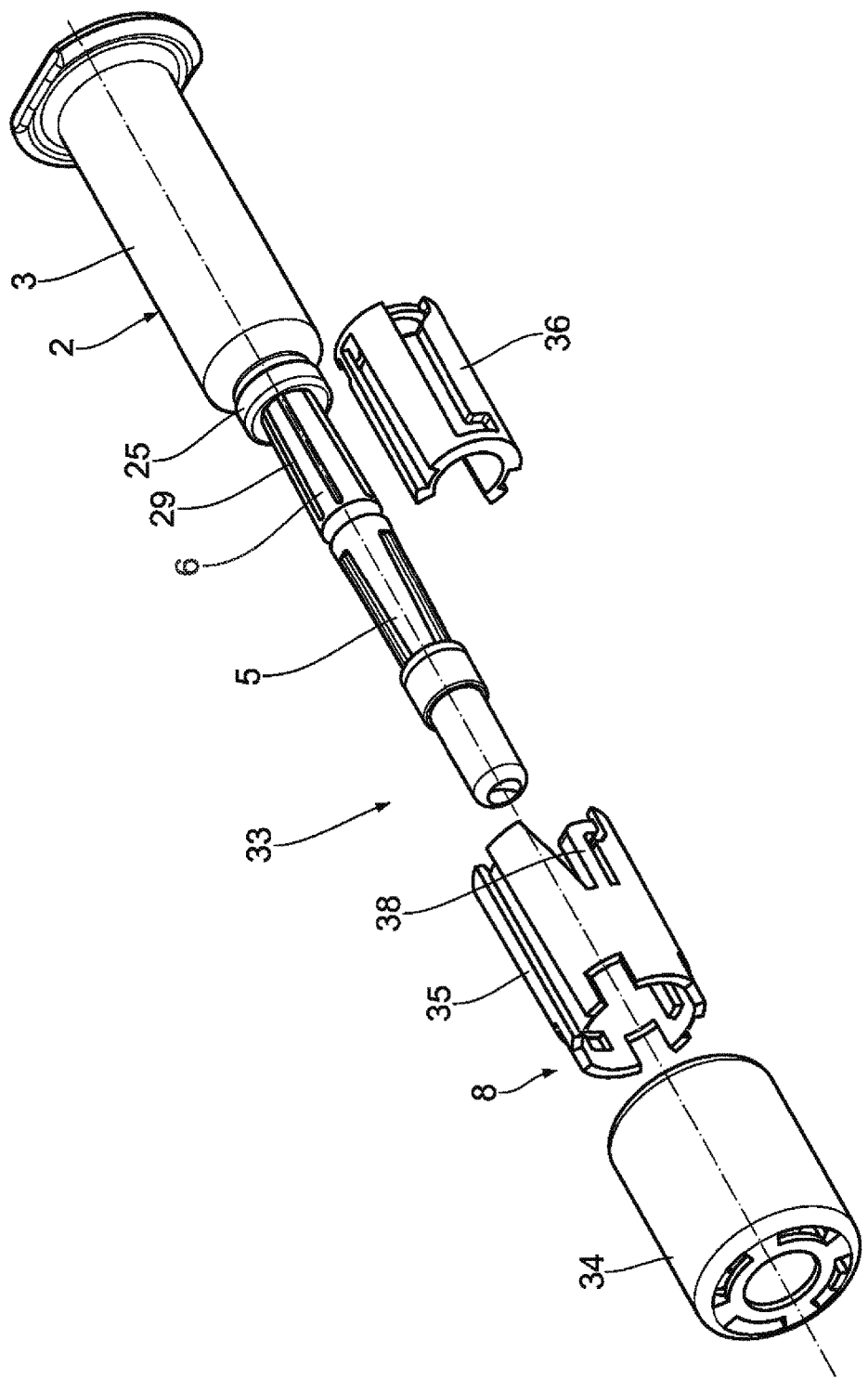
FIG. 12 an exploded illustration of a further embodiment of a medical injection device having a telescoping needle guard.
Figure 13:
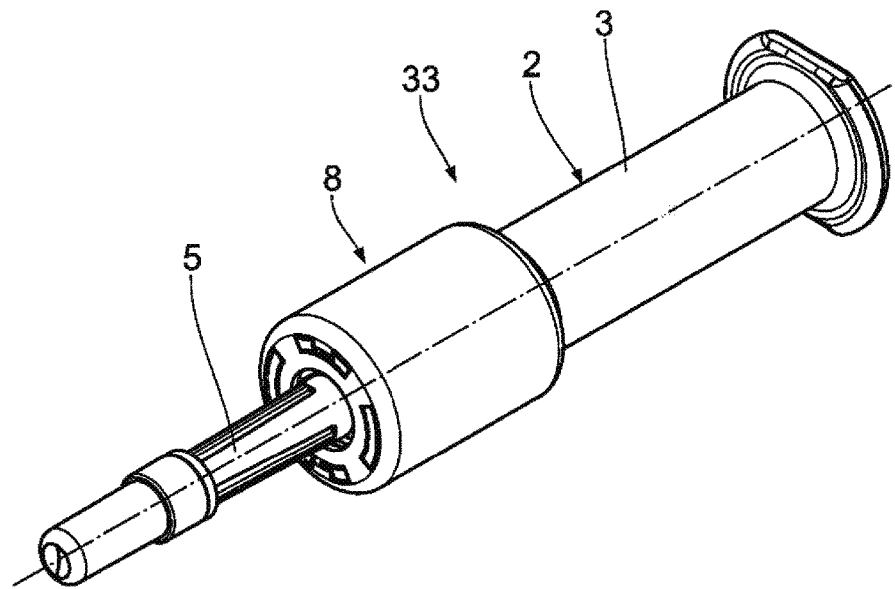
FIG. 13 the injection device according to FIG. 12 with the needle guard in the injection position.
Figure 14:
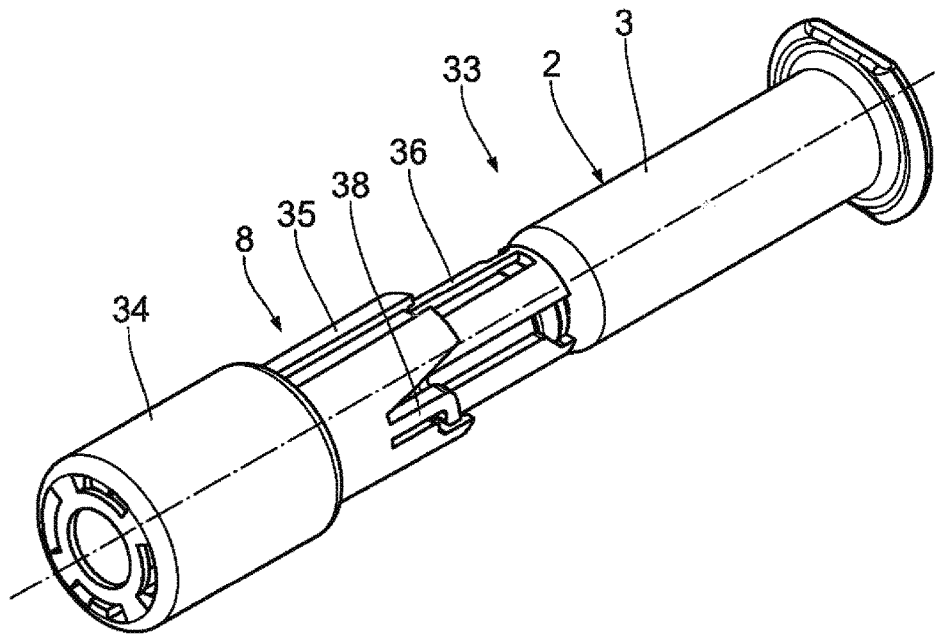
FIG. 14 the injection device according to FIG. 12 with the needle guard in the safe position.
Figure 18:
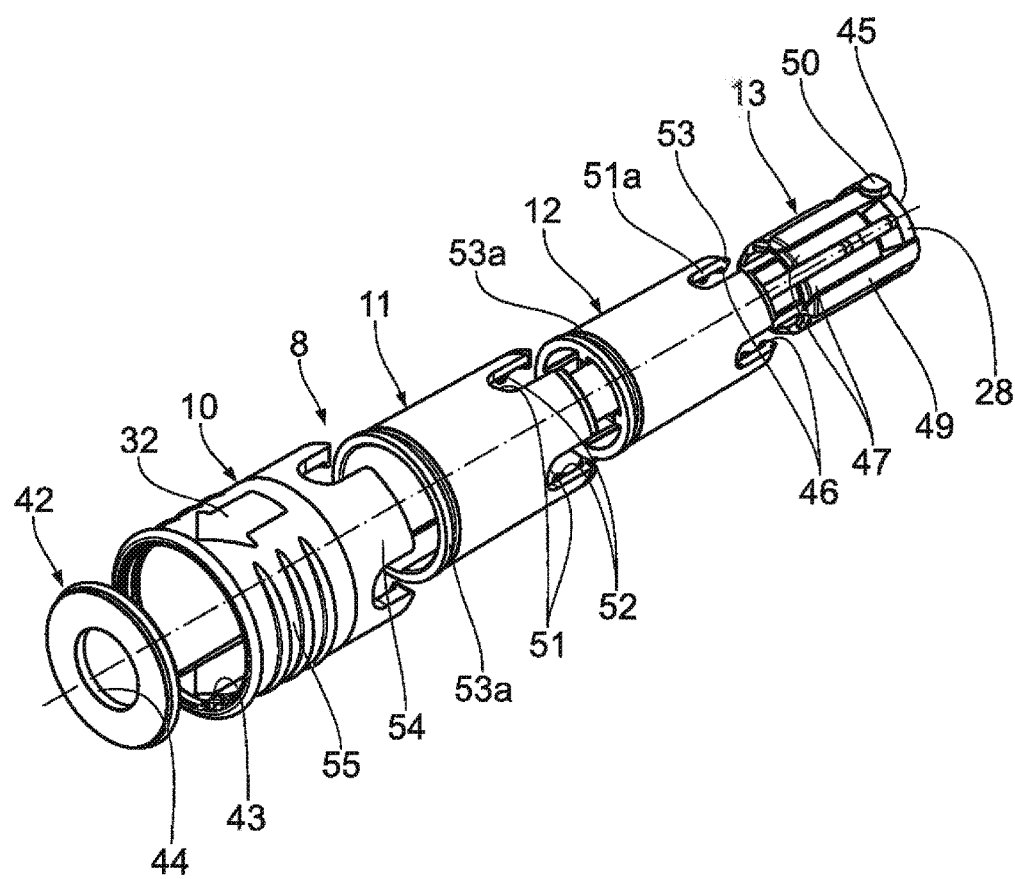
FIG. 18 an exploded illustration of a further embodiment of a telescoping needle guard for a medical injection device.
Figure 19:
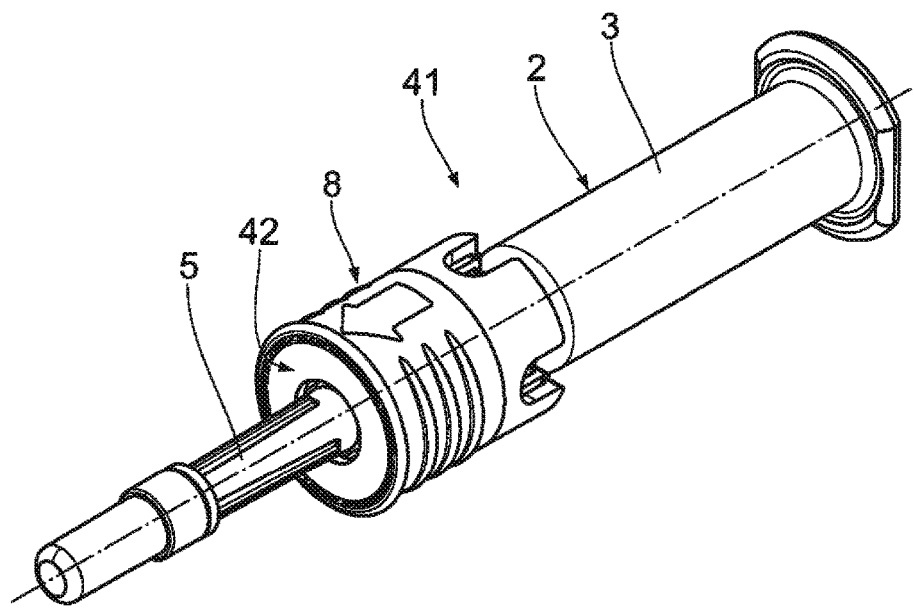
FIG. 19 an injection device with the needle guard according to FIG. 18 in the injection position.
Figure 20:
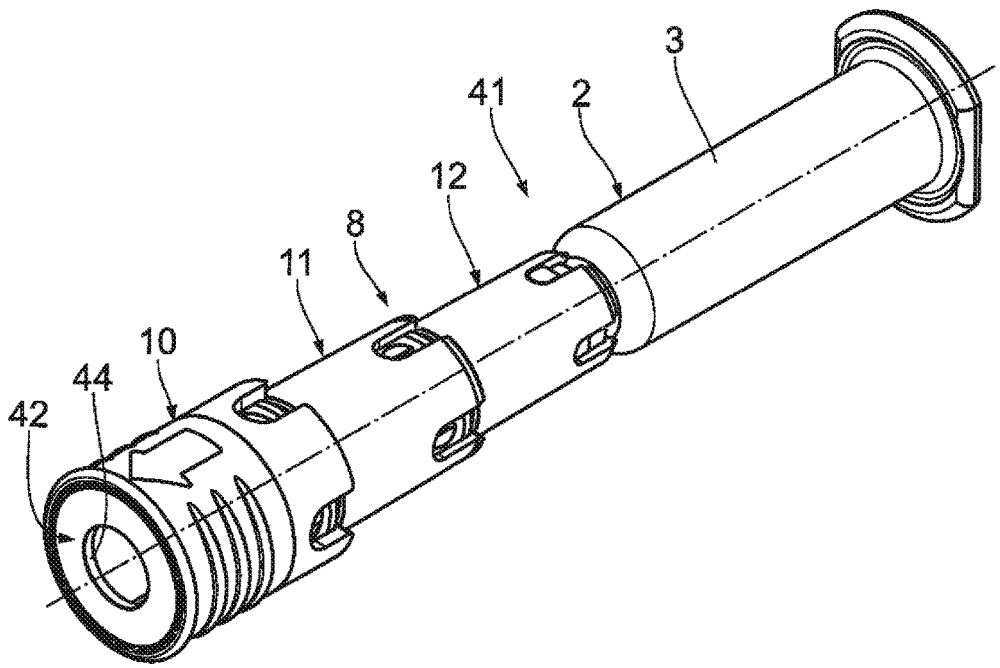
FIG. 20 the injection device according to FIG. 18 with the needle guard in the safe position.
Figure 23:
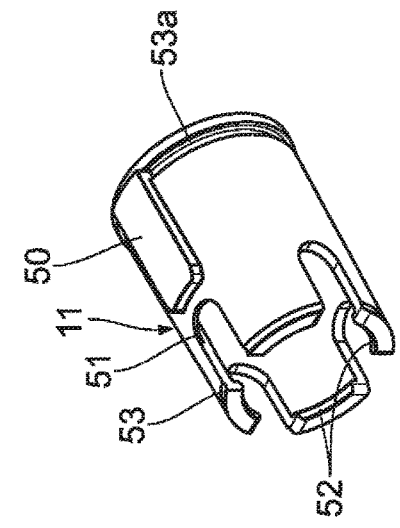
FIG. 23 a central telescoping sleeve of the needle guard according to FIGS. 18 to 20, arranged between the connecting telescoping sleeve according to FIG. 22 and a protective telescoping sleeve of the needle guard.
Figure 24:
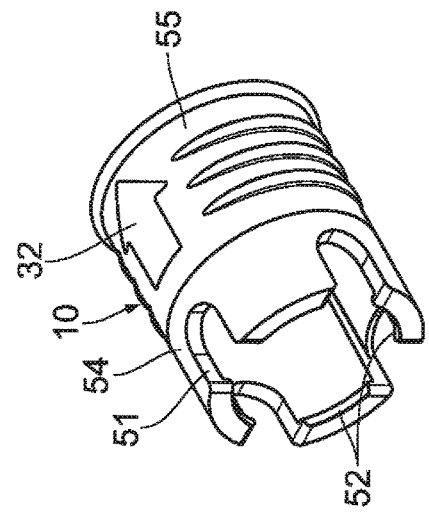
FIG. 24 the protective telescoping sleeve of the needle guard according to FIGS. 18 to 20.
Figure 21:
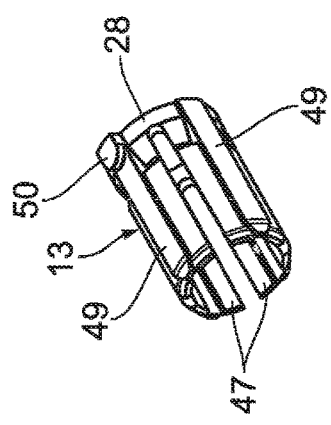
FIG. 21 an interlocking adapter for connecting the needle guard according to FIGS. 18 to 20 to the syringe in an interlocking manner.
Figure 22:
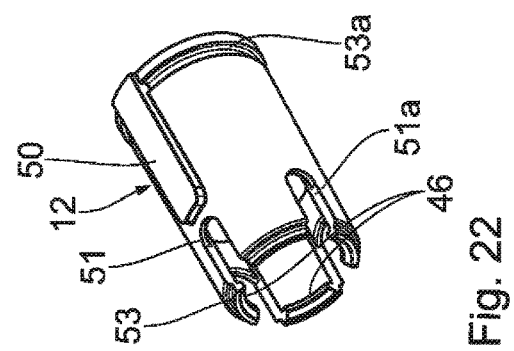
FIG. 22 a connecting telescoping sleeve of the needle guard according to FIGS. 18 to 20, arranged between the interlocking adapter according to FIG. 21 and a central telescoping sleeve of the needle guard.
Figure 25:
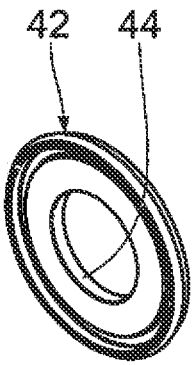
FIG. 25 an annular cover for the protective telescoping sleeve according to FIG. 24.
Figure 26:
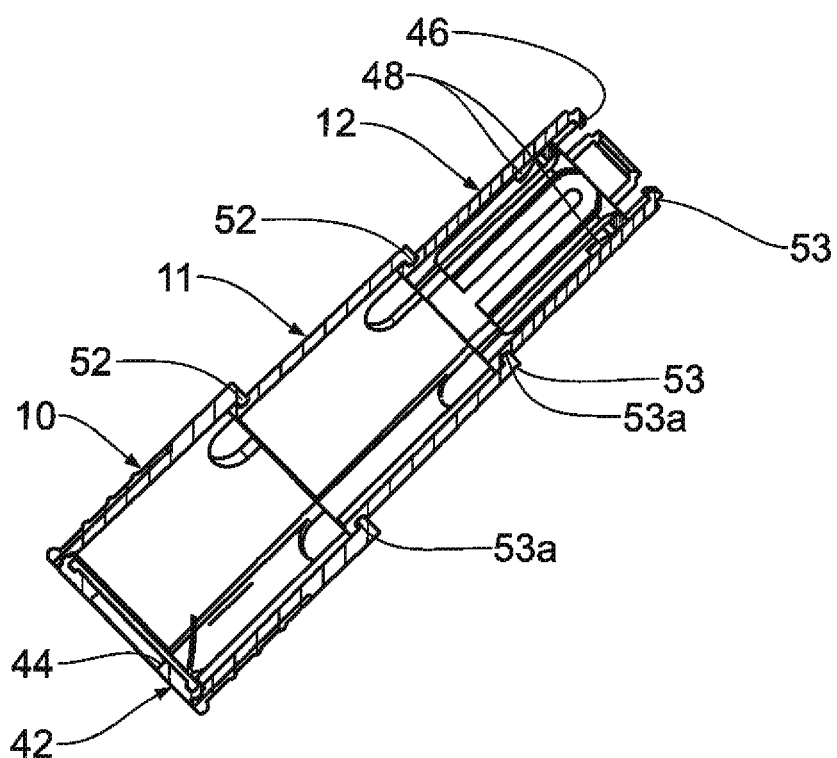
FIG. 26 an axial longitudinal cross-section of the needle guard according to FIGS. 18 to 20, shown in the safe position.
Figure 27:
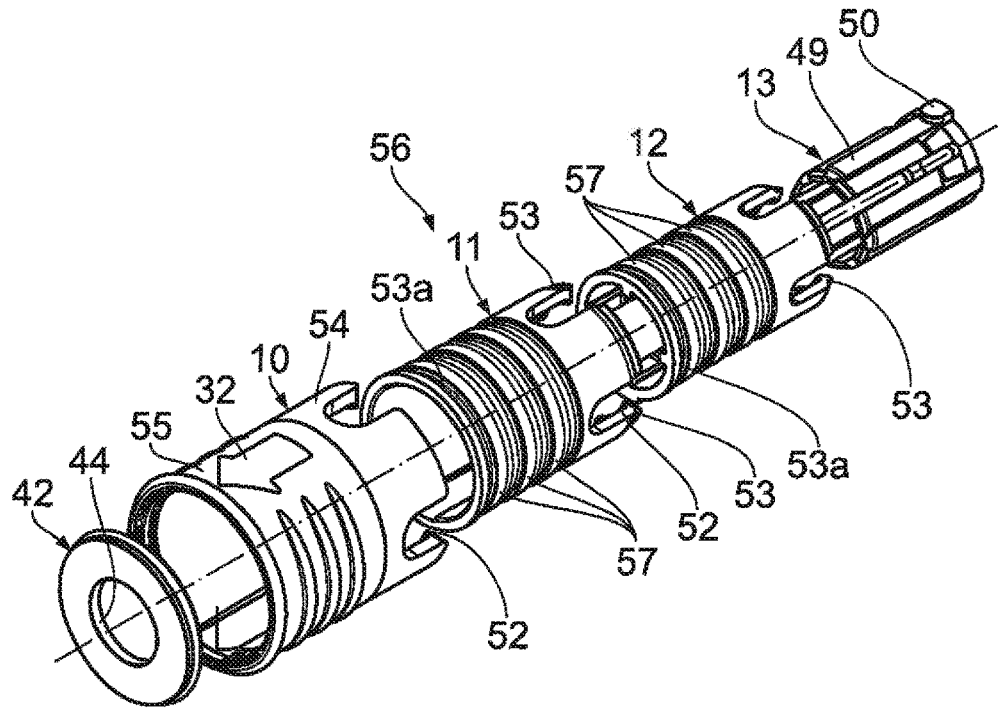
Figure 28:
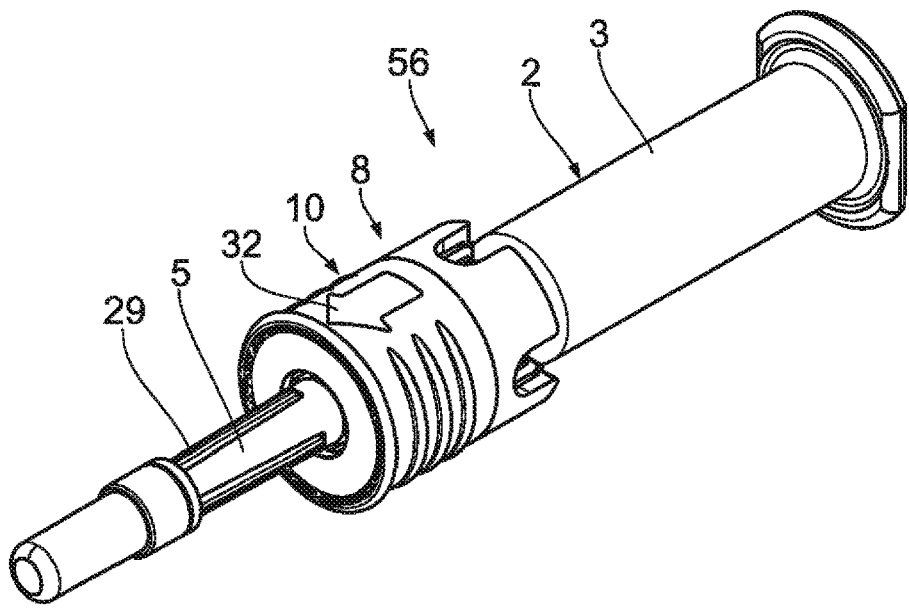
Figure 29:
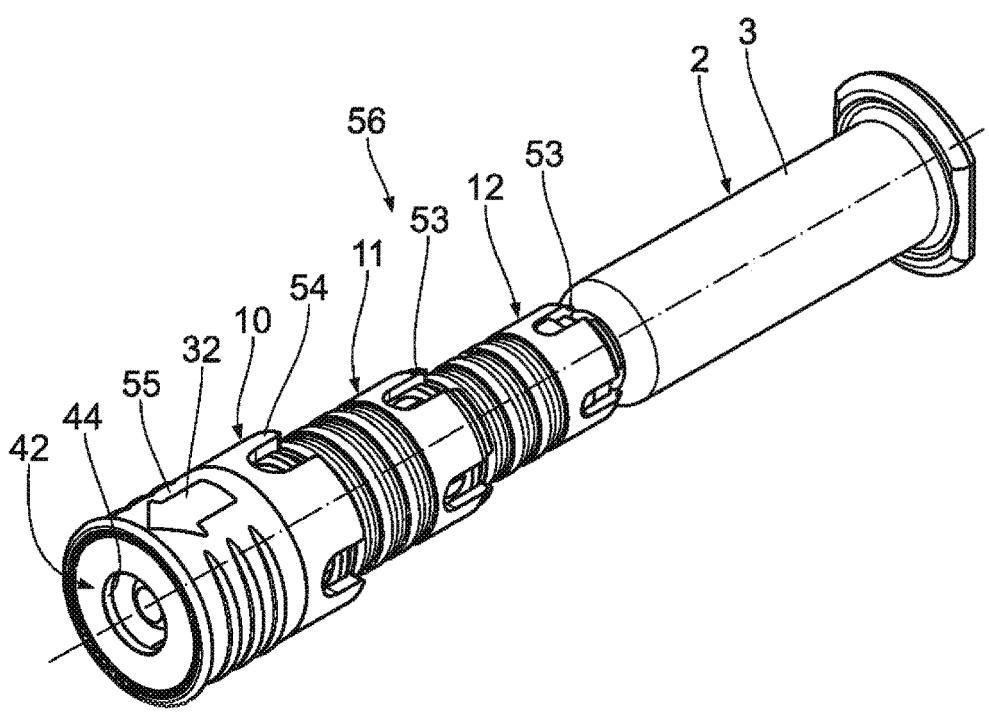
Figure 34:
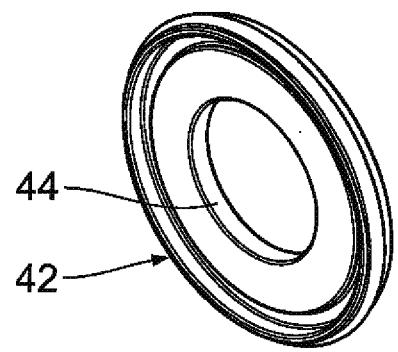
Figure 35:
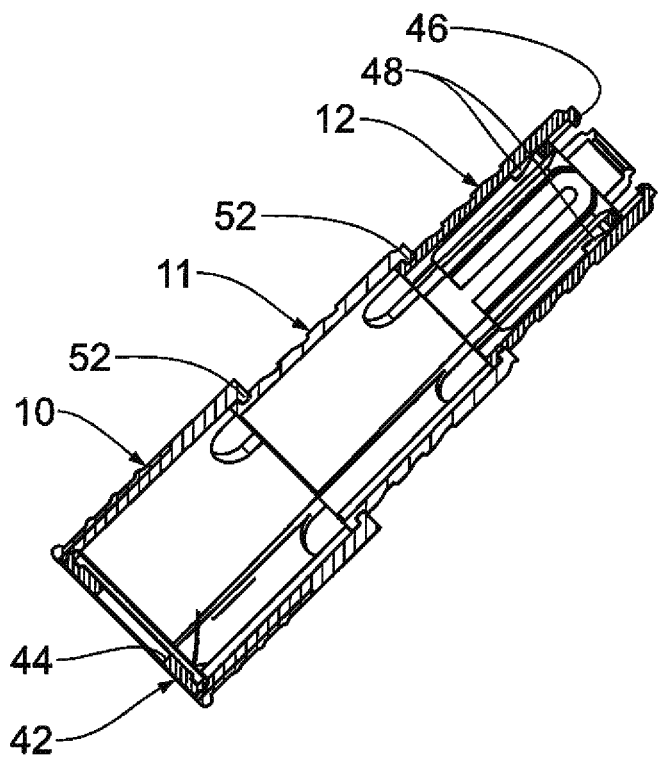
Figure 36:
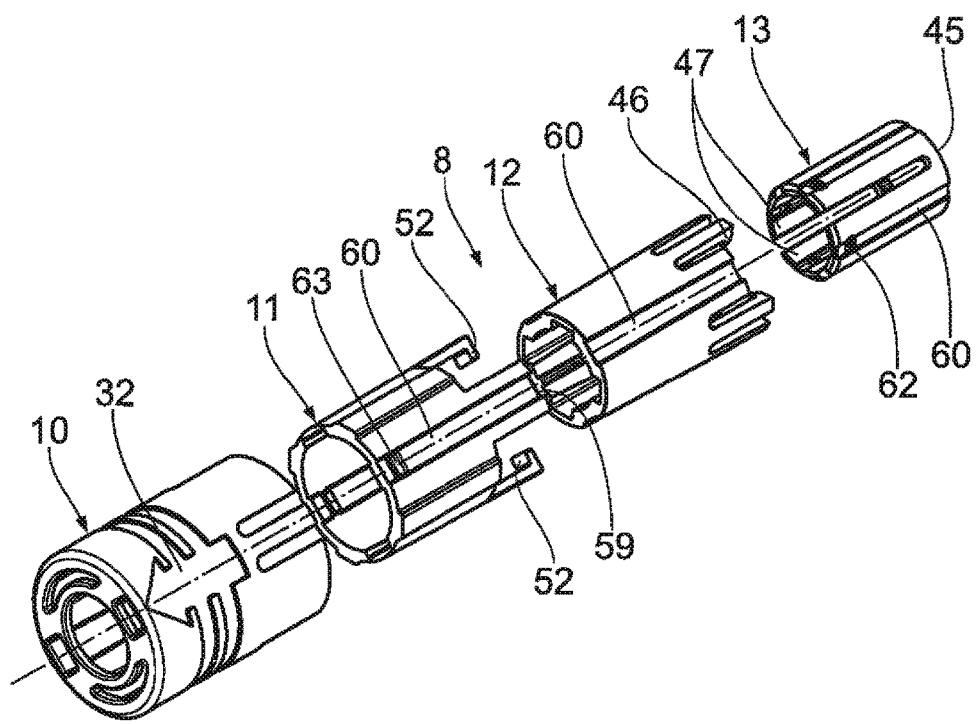
FIGS. 36 to 42 illustrations similar to those of FIGS. 18 to 24 of components of a further embodiment of a needle guard for a syringe.
Figure 37:
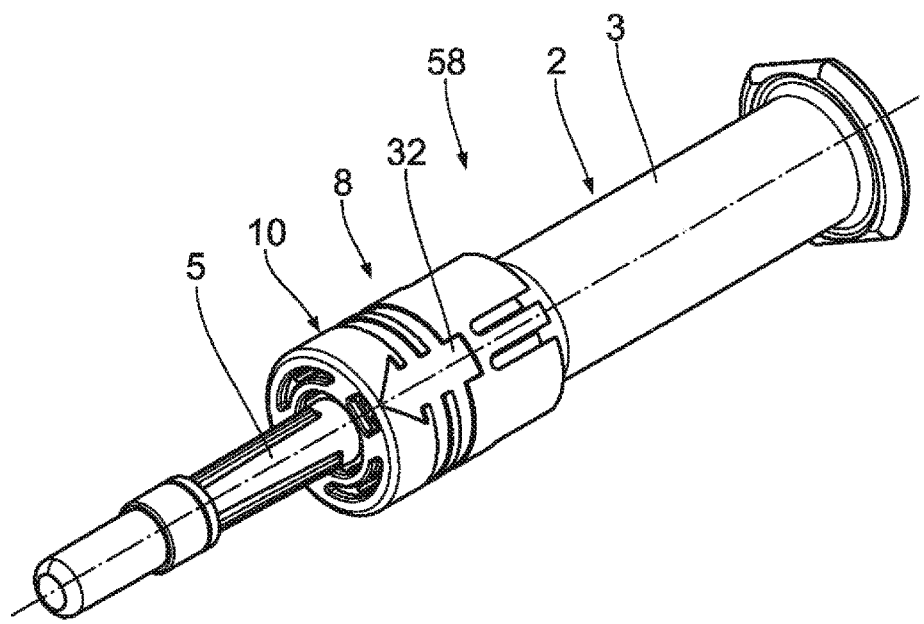

After assembly, injection device 1 with needle guard 8 is in the injection position, and safety cap 5, which was originally attached, projects beyond injection needle 4, as shown in FIGS. 1 and 11. The various rotation prevention components prevent the total of four components 10 to 13 of needle guard 8 from rotating relative to one another, and also prevent needle guard 8 as a whole from rotating relative to syringe 2.

Injection device 1 is used as follows: First, safety cap 5 is removed from injection cannula 4 by a twist-off movement (cf. arrow 30 in FIG. 1). During the twist-off movement, the cross-sectional shape of protective telescoping sleeve 10, which projects beyond the outer circumference of container 3, ensures that the user will grasp the injection device 1 on the outside of protective telescoping sleeve 10 in order to twist off safety cap 5. For this purpose, protective telescoping sleeve 10 has longitudinal ribs that extend axially and prevent protective telescoping sleeve 10 from rotating unintentionally between the user's fingers as he is twisting off safety cap 5. Since all the components of needle guard 8 are prevented from rotating relative to one another and since interlocking adapter 13 is prevented from rotating relative to opening section 6, when safety cap 5 is rotated relative to needle guard 8 in the direction of arrow 30 (or in the opposite direction), safety cap 5 will reliably be twisted off as desired from opening section 6. Once it has been twisted off, the safety cap 5 can be removed from the injection cannula 4.

Figure 2:
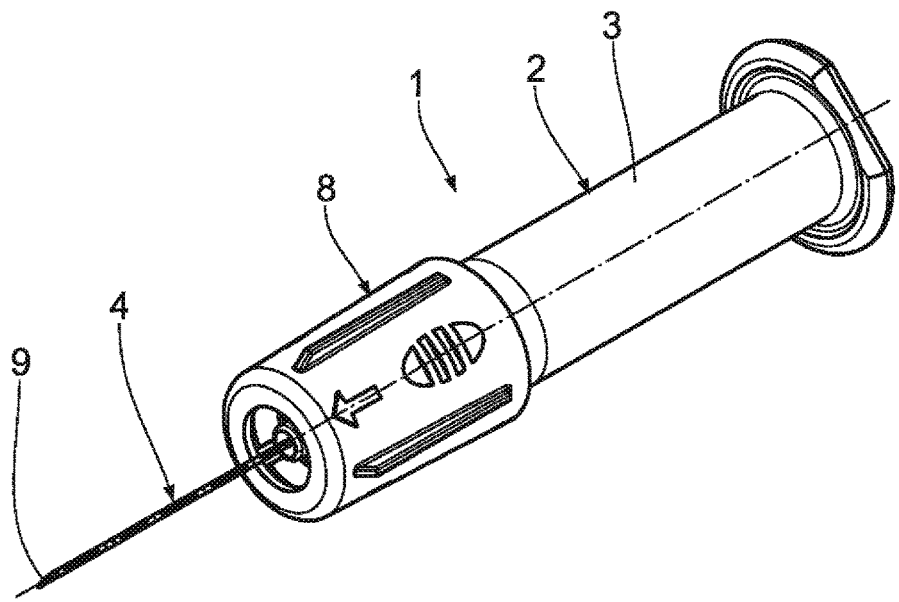
FIG. 2 the injection device according to FIG. 1 ready for use, in which state an original safety cap has been removed from an injection cannula.
Figure 3:
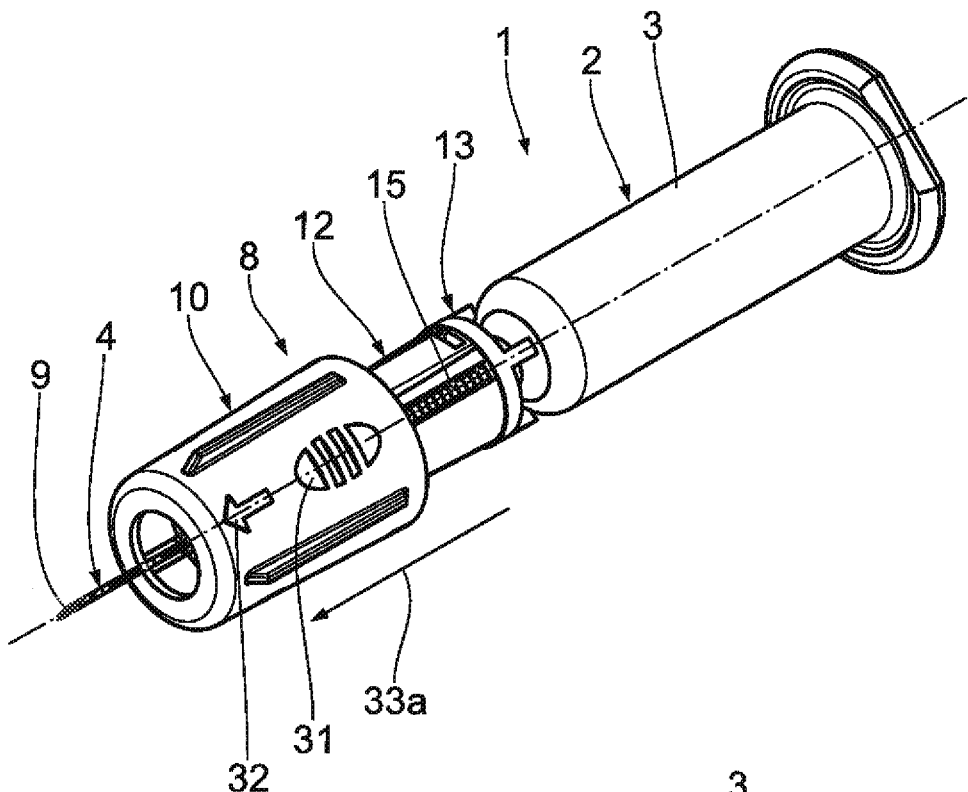
FIG. 3 the injection device according to FIG. 2 during movement of the telescoping needle guard between an injection position, as shown in FIGS. 1 and 2, in which the injection cannula can be uncovered (FIG. 1) or is uncovered (FIG. 2) for injecting a medium, and a safe position, in which a cannula tip of the injection cannula is recessed in a protective component of the telescoping needle guard.
Figure 4:
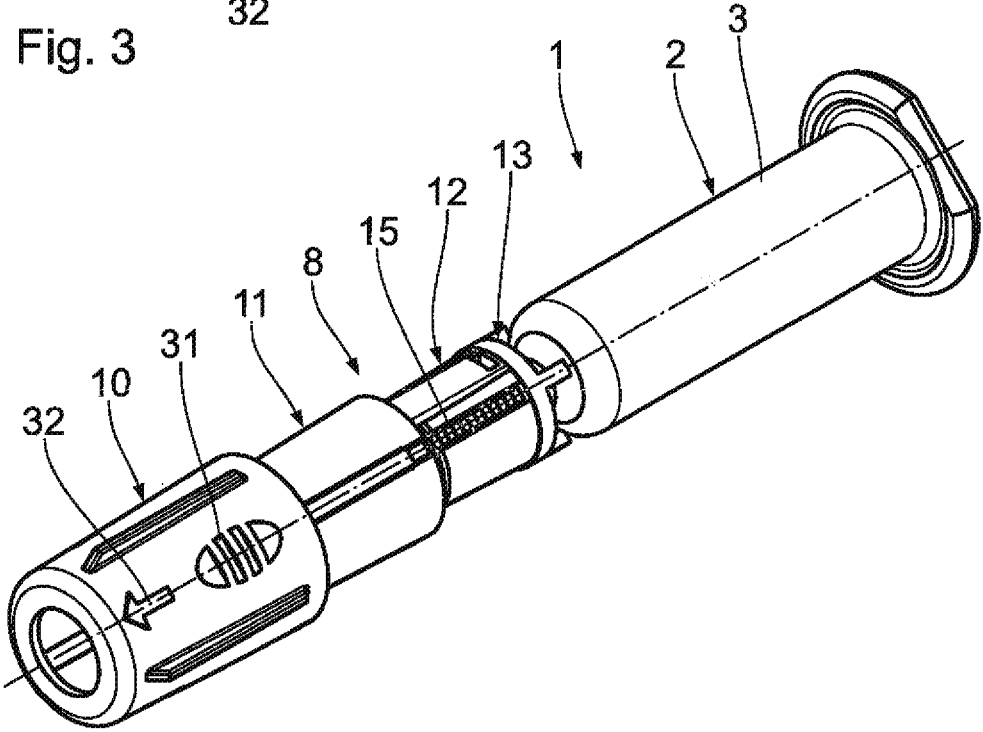
FIG. 4 the injection device with the telescoping needle guard in the safe position.

Injection device 1 is then ready for use, as shown in FIG. 2. To move needle guard 8 to the safe position (cf. FIGS. 3 to 7), pressure is first exerted from both sides on protective telescoping sleeve 10 in a pressure region 31, which is marked on outer protective telescoping sleeve 10. This releases the opposing locking elements 17 from the latching hooks 24, and allows outer protective telescoping sleeve 10 to be extended axially in the direction of arrow 32 applied there, relative to telescoping sleeve 11 (cf. arrow 33*a* in FIG. 3). This causes opposing locking element 17 to rattle over the locking teeth 16 of guard locking assembly 14 until the opposing locking element 17 reaches its end position, upstream of the final locking tooth 16' of center telescoping sleeve 11. Center telescoping sleeve 11 then also extends relative to inner connecting telescoping sleeve 12, wherein the opposing locking elements 18 of center telescoping sleeve 11 rattle over the locking teeth 16 of inner connecting telescoping sleeve 12 until in this case as well, the end position of opposing locking element 18 has reached the final locking tooth of inner connecting telescoping sleeve 12. Needle guard 8 is then in the fully extended safe position, shown in FIG. 4. In this position, cannula tip 9 of injection cannula 4 is fully recessed in protective telescoping sleeve 10, thereby ensuring a safe needle guard. Due to the one-way character of the dedicated locking assemblies 14, a user cannot move needle guard 8 out of the safe position shown in FIG. 4 to again uncover cannula tip 9 without destroying the guard.

In the following, a further embodiment of an injection device 33 will be specified in greater detail in reference to FIGS. 12 to 17. Components and functions that correspond to those already described in reference to FIGS. 1 to 11 are identified by the same reference signs, and will not be discussed again in detail.

Needle guard 8 of injection device 33 according to FIGS. 12 to 17 also has three telescoping sleeves, namely an outer protective telescoping sleeve 34, the function of which corresponds to that of protective telescoping sleeve 10 of the embodiment according to FIGS. 1 to 11, a center telescoping sleeve 35, the function of which corresponds to that of telescoping sleeve 11 of the embodiment of FIGS. 1 to 11, and an inner, connecting telescoping component 36, which also functions as an interlocking adapter for connecting needle guard 8 to syringe 2 in an interlocking manner. Connecting telescoping component 36 therefore combines the functions of inner telescoping sleeve 12 and interlocking adapter 13 of the embodiment according to FIGS. 1 to 11.

Connecting telescoping component 36 is embodied as a C-shaped adapter that can be snapped on radially. Connecting telescoping component 36 is snapped radially onto opening section 6 of container 3, wherein to secure connecting telescoping component 36 axially, the connecting telescoping component 36 engages behind locking collar 25 of opening section 6 in a circumferential region.

To ensure better frictional contact between connecting telescoping component 36 and opening section 6 of container 3 of syringe 2, and therefore particularly to prevent rotation, inner ribs 37 of connecting telescoping component 36, which when assembled come to rest between the peripheral ribs 29 of opening section 6, are made of softer plastic material than the rest of the base body of connecting telescoping component 36. The ribs 37 can be formed on the base body of connecting telescoping component 36, for example, by a multicomponent technique, more particularly, by a 2-component technique. One of these inner ribs 37 is shown in FIG. 15. Actually, a plurality of ribs 37, e.g. five, lies evenly spaced in the circumferential direction, with the spacing adapted to the circumferential distance between the peripheral ribs 29.

Center telescoping sleeve 35 (cf. FIG. 16) is connected to connecting telescoping component 36 via a radially acting locking connection. For this purpose, center telescoping sleeve 35 has a spring-mounted tongue 38, which engages in a corresponding locking recess in connecting telescoping component 36.

Outer protective telescoping sleeve 34 likewise has a spring-mounted tongue 39, which engages in a corresponding locking recess in center telescoping sleeve 35 and/or in connecting telescoping assembly 36 to form a locking connection. Spring-mounted tongue 39 and the dedicated locking recess in the injection position therefore form the injection connecting assembly for securing telescoping protective sleeve 34 on syringe 2 in the injection position in an interlocking manner.

In the embodiment shown in FIGS. 12 to 17, when needle guard 8 is in the safe position, locking tongue 39 engages in a locking recess 40, which is formed in center telescoping sleeve 35. In this manner, and by means of a corresponding locking connection of center telescoping sleeve 35 on connecting telescoping component 36, a guard locking assembly is created for locking protective telescoping sleeve 34 in the safe position.

Apart from the differences described above, the assembly and use of injection device 33 correspond to the above description referring to injection device 1.

In the following, a further embodiment of an injection device 41 will be specified in greater detail in reference to FIGS. 18 to 26. Components and functions that correspond to those already described in reference to injection devices 1 and 33 are identified by the same reference signs, and will not be discussed again in detail.

Injection device 41 likewise has a telescoping needle guard 8, which is designed as comprising a connecting telescoping sleeve 12, an interlocking adapter 13, a center telescoping sleeve 11 and a protective telescoping sleeve 10 in essentially the same design as the guard 8 of injection device 1. Differences exist in the details of the locking connections and the guide structures. The locking connections in injection device 41 are designed as axial locking connections.

Protective telescoping sleeve 10 in needle guard 8 of injection device 41 is designed as having two parts, and has a ring-shaped cover 42 in addition to the actual telescoping sleeve. Cover 42 snaps into an inner circumferential groove 43 in an outer end region of protective telescoping sleeve 10, over an outer circumference. An annular snap-in connection between cover 42 and protective telescoping sleeve 10 is formed by the outer periphery of cover 42 and inner circumferential groove 43. Cover 42 serves to reduce the opening width of protective telescoping sleeve 10 that is accessible from the outside to a through opening 44 having a reduced diameter as compared with the inner diameter of the rest of protective telescoping sleeve 10.

To assemble needle guard 8 according to FIGS. 18 to 26, first center telescoping sleeve 11 is inserted into protective telescoping sleeve 10, which is still without a cover, from the side of inner circumferential groove 43. Connecting telescoping sleeve 12 is then inserted into center telescoping sleeve 11 from the same side. Cover 42 is then snapped into inner circumferential groove 43. And interlocking adapter 13 is inserted into connecting telescoping sleeve 12 from the opposite end.

Once the needle guard has been preassembled in this manner, it can be pushed onto syringe 2. It is pushed on until a mating collar 45 of interlocking adapter 13 rests on locking collar 25 of syringe 2 (cf., e.g., FIG. 8).

As needle guard 8 according to FIGS. 18 to 26 is pushed further onto syringe 2 in the direction of container 3, connecting telescoping sleeve 12 is moved axially up to interlocking adapter 13, which is then fixed axially on locking collar 25, until latching hooks 46, which are formed on connecting telescoping sleeve 12, engage behind locking collar 25 of opening section 6 of syringe 2. Thus injection device 41 uses latching hooks 46 on connecting telescoping sleeve 12, rather than latching hooks on interlocking adapter 13, for example, to fix protective telescoping sleeve 10 as a protective component of needle guard 8 on syringe 2 in the injection position, in an interlocking manner.

Injection device 41 also has means for preventing rotation between needle guard 8, which therefore is also a rotation prevention device, and opening section 6 of syringe 2. For this purpose, interlocking adapter 13 of injection device 41 is in turn equipped with rotation prevention tongues 47, which correspond to locking tongues 27 of the embodiment according to FIGS. 1 to 11. The rotation prevention tongues 47 extend axially and are connected to one another via ring support 28 of interlocking adapter 13 of injection device 41. Each of the rotation prevention tongues 47 is mounted so as to be held between two adjacent, axially extending peripheral ribs 29 in opening section 6 of syringe 2.

A retention means formed on connecting telescoping sleeve 12 holds rotation prevention tongues 47 down between peripheral ribs 29. Said means is formed by a total of four inner axial ribs, two of which are visible in the axial cross-section of FIG. 26. Each of axial ribs 48 are formed offset 90° in the circumferential direction on an inner wall of connecting telescoping sleeve 12. Each of axial ribs 48 interacts with an opposite retaining piece on interlocking adapter 13 in order to hold down one rotation prevention tongue 47. The opposing retaining pieces are formed by outer axial ribs 49 on interlocking adapter 13 (cf. FIG. 21).

Interlocking adapter 13 is secured against rotation on connecting telescoping sleeve 12, and two adjoining telescoping sleeves 12, 11, 10 are secured against relative rotation around the longitudinal axis of needle guard 8, each by rotation prevention means. Said rotation prevention means are in turn formed by outer tongues 50, each on one of components 13, 12 and 11, which interact with complementary inner axial grooves 51 in the respective adjacent outer telescoping sleeves 12, 11, 10, to prevent rotation.

The tongues 50 serve simultaneously as stops, which interact with axially extending recesses 51a as stops in order to establish the axial end position of connecting telescoping sleeve 12 relative to interlocking adapter 13 in the locking connection of needle guard 8 to locking collar 25 of opening section 6 via latching hooks 46 of connecting telescoping sleeve 12.

Similarly to latching hooks 46 of connecting telescoping sleeve 12, center telescoping sleeve 11 and protective telescoping sleeve 10 also have comparable, radially acting latching hooks 52. The latching hooks 52 are also arranged offset from one another 90° in the circumferential direction, in the same manner as latching hooks 46. In the injection position shown in FIG. 19, for example, latching hooks 46 and 52 of adjacent telescoping sleeves 12, 11, 10 lie precisely one above the other. The latching hooks 52 of center telescoping sleeve 11 then engage behind complementary recesses 53 in the outer side of latching hooks 46. The latching hooks 52 of protective telescoping sleeve 10 engage behind corresponding recesses 53 in the outer side of latching hooks 52 of center telescoping sleeve 11.

When needle guard 8 is in the safe position (cf. e.g. FIGS. 20 and 26), the latching hooks 52 of center telescoping sleeve 11 on one side, and of protective telescoping sleeve 10 on the other side interact with outer peripheral grooves 53a in connecting telescoping sleeve 12 on one side and in center telescoping sleeve 11 on the other side.

When the telescoping sleeves 11, 10 are moved from the collapsed injection position to the extended safe position, the latching hooks 52 slide between the respective opposing recesses 53 and the peripheral grooves 53a. In order for a uniform amount of force to be applied to the latching hooks 52 when telescoping sleeves 11 and 10 are moved to the safe position, telescoping sleeves 12 and 11 expand conically between the opposing recesses 53 and the respective peripheral grooves 53a.

Protective telescoping sleeve 10 is embodied as a 2-component injection-molded part. In addition to supporting piece 54, protective telescoping sleeve 10 has a grip section 55. The supporting piece 54 on one side and the grip section 55 on the other side are embodied as different injection-molded components of the 2-component parts. In 2-component plastics, ABS (acrylonitrile-butadiene styrene) can be used for a hard component, for example, for the supporting piece 54, and TPE (thermoplastic elastomer) can be used for a soft component, for example, for the quick section 55. A different number of components can also be used with such a multicomponent injection-molded part, for example, three or more components made of different plastics, particularly of plastics having different hardnesses.

Forming the protective telescoping sleeve 10 as a 2-component injection-molded part ensures better non-slip characteristics of the protective telescoping sleeve 10 in the region of the grip section 55.

The axial ribs 48 of connecting telescoping sleeve 12 that serve as retaining means can also be made of a different plastic material from the other connecting telescoping sleeve 12, and the axial ribs 48 can be formed by a 2-component injection-molding technique on another supporting piece of connecting telescoping sleeve 12.

In the following, a further embodiment of an injection device 56 will be specified in greater detail in reference to FIGS. 27 to 35. Components and functions that correspond to those already described in reference to injection devices 1, 33 and 41 and particularly in reference to injection device 41 are identified by the same reference signs, and will not be discussed again in detail.

Between opposing recesses 53 and peripheral grooves 53a, connecting telescoping sleeve 12 and center telescoping sleeve 11 each have three locked intermediate stages 57. When protective telescoping sleeve 10 and center telescoping sleeve 11 are moved between the injection position and the safe position, the respective latching hooks 52 of protective telescoping sleeve 10 and center telescoping sleeve 11 lock along their path of movement between the respective opposing recesses 53 and the respective peripheral grooves 53a via the locked intermediate stages 57. The user receives a haptic indication of the path that has been traveled by the two telescoping sleeves 10, 11 between the injection position and the safe position.

In the following, a further embodiment of an injection device 58 will be specified in greater detail in reference to FIGS. 36 to 43. Components and functions that correspond to those described above in reference to injection devices 1, 33, 41 and 56 are identified by the same reference signs, and will not be discussed again in detail.

Similarly to injection device 1, injection device 58 is embodied in four parts, with an inner interlocking adapter 13, a connecting telescoping sleeve 12, a center telescoping sleeve 11 and an outer protective telescoping sleeve 10.

In injection device 58, the function of latching hooks 46 and 52 of telescoping sleeves 12, 11 and 10 is similar to that of injection device 41. Telescoping sleeves 11 and 10 each have two opposing latching hooks 52, which are therefore arranged offset 180° from one another in the circumferential direction. When injection device 8 is assembled, the latching hooks 52 of center telescoping sleeve 11 are offset 90° in the circumferential direction relative to latching hooks 52 of protective telescoping sleeve 10, similarly to the design of the opposing locking elements and the locking teeth of injection device 1.

For assembly, center telescoping sleeve 11 is first inserted into outer protective telescoping sleeve 10 in the direction of arrow 32, until the latching hooks 52 of outer protective telescoping sleeve 10 engage in opposing recesses 59 in center telescoping sleeve 11, which are formed at the end of axial guide tracks 60 in an outer wall of center telescoping sleeve 11.

Connecting telescoping sleeve 12 is then likewise inserted into center telescoping sleeve 11 in the direction of arrow 32. Insertion continues until the latching hooks 52 of center telescoping sleeve 11 come to rest in recesses 61 in connecting telescoping sleeve 12, which are in turn formed at the end of axial guide tracks 60 in an outer wall of connecting telescoping sleeve 12.

Interlocking adapter 13 is then inserted, again in the direction of arrow 32, into connecting telescoping sleeve 12 until latching hooks 46 of connecting telescoping sleeve 12 engage from the outside in recesses 62 in interlocking adapter 13. The recesses 62 are in turn formed in axial guide tracks 60 of interlocking adapter 13. In this preassembled position, sleeves 11 and 12 are disposed nearly completely inside outer protective telescoping sleeve 10. Interlocking adapter 13 projects with the majority of its axial extension between the recesses 62 and the mating collar 45 beyond collapsed telescoping sleeves 10 to 12.

To mount preassembled needle guard 8 on syringe 2, needle guard 8 and guiding interlocking adapter 13 are pushed onto the opening section 6 of syringe 2 until mating collar 45 reaches locking collar 25 of opening section 6. The three collapsed telescoping sleeves 10 to 12 are then moved further in the axial direction toward container 3, wherein the latching hooks 46 of connecting telescoping sleeve 12 back out of the recesses 62 in interlocking adapter 13, slide along the guide tracks 60, and then engage behind locking collar 25 to secure needle guard 8 on syringe 2. At the same time, retaining means again ensure that the rotation prevention tongues 47 of interlocking adapter 13 are held down between adjacent peripheral ribs 29 of opening section 6 to prevent the rotation of needle guard 8 on syringe 2.

The interaction of the guide tracks 60 with the assigned latching hooks 46, 52 serves to prevent rotation of the components of needle guard 8 relative to one another. Further rotation prevention is provided by axial guides, each offset 90° from the latching hook/guide track constructions.

Needle guard 8 is then ready in the injection position.

Figure 38:
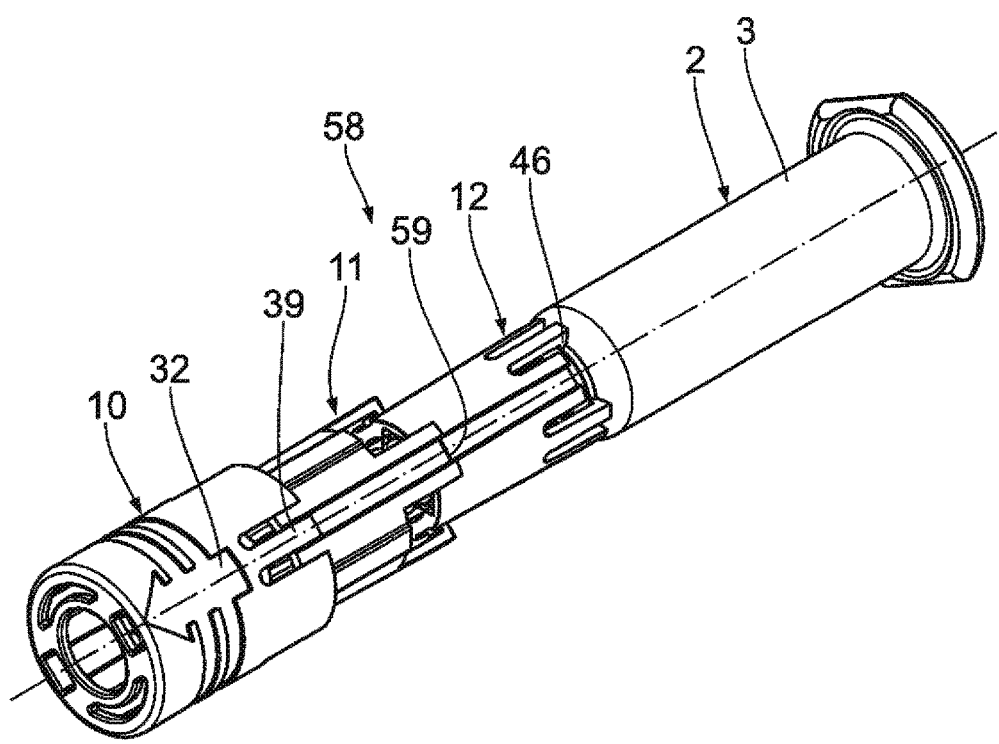
Figure 41:
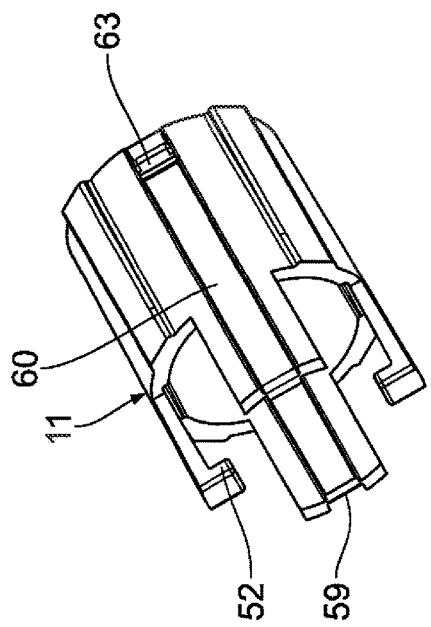
Figure 42:
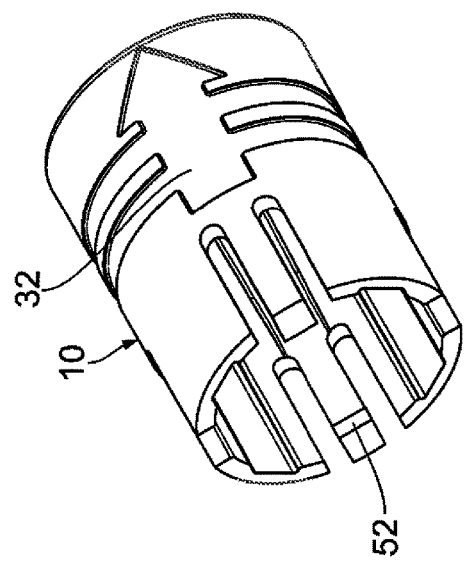
Figure 39:
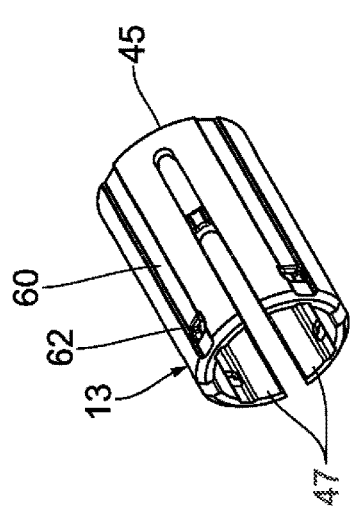
Figure 40:
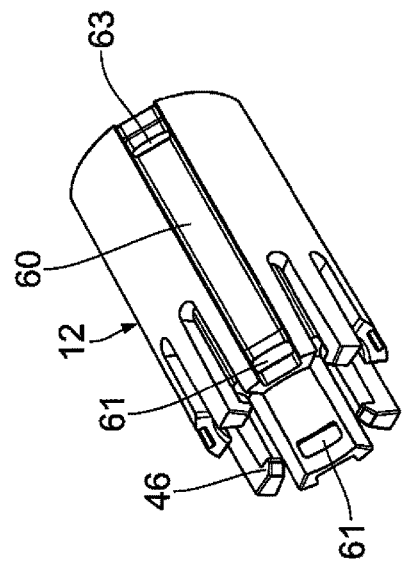
Figure 43:
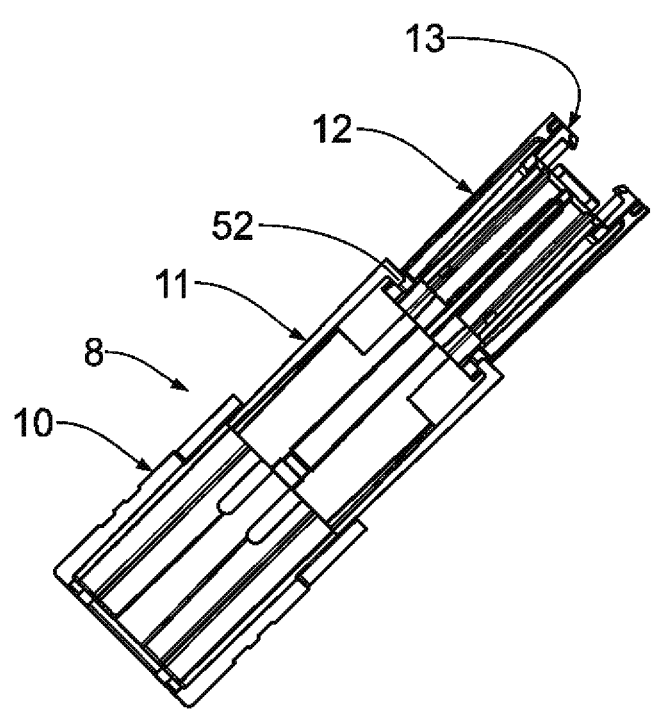
FIG. 43 an axial longitudinal cross-section of the needle guard according to FIGS. 36 to 38, shown in the safe position.

When needle guard 8 is moved from the injection position to the safe position, the latching hooks 52 of center telescoping sleeve 11 back out of the recesses 61 of connecting telescoping sleeve 12 on one side, and the latching hooks 52 of outer protective telescoping sleeve 10 back out of the opposing recesses 59 of center telescoping sleeve 11 on the other side. The latching hooks of telescoping sleeves 10 and 11 then run axially along the respective guide tracks 60 of telescoping sleeves 11 and 12 until the latching hooks 52 of outer protective telescoping sleeve 10 slide into recesses 63 that are formed at ends of the guide tracks 60 opposite the opposing recesses 59. In the safe position, the latching hooks 52 of center telescoping sleeve 11 slide further into recesses 63 which are formed in the guide tracks 60 of connecting telescoping sleeve 12 at the ends opposite the recesses 61. Thus the telescoped safe position shown in FIG. 38 or 43 is reached.

The invention claimed is:

1. A medical injection device comprising:
   a syringe, comprising:
      a container for a medium to be injected, and
      an injection cannula, which communicates with the container,
   a needle guard, which can be moved between
      an injection position, in which the injection cannula can be opened up to inject the medium, and
      a safe position, in which a cannula tip of the injection cannula is arranged recessed in a protective component of the needle guard, and
      a securing device for securely fixing the protective component when the needle guard is in the safe position, and
   an interlocking adapter for connecting the needle guard to the syringe in an interlocking connection;
   wherein the needle guard has at least three telescoping sleeves, wherein one of the telescoping sleeves is a connecting telescoping sleeve that is connected to the syringe,
   wherein a second of the telescoping sleeves is a protective telescoping sleeve that forms the protective component, and
   wherein at least a third of the telescoping sleeves is arranged between the connecting telescoping sleeve and the protective telescoping sleeve;
   wherein the interlocking adapter is configured as an adapter sleeve which is a separate part arranged in between the syringe and the connecting telescoping sleeve; and
   wherein the interlocking adapter is arranged within the needle guard.

2. The injection device according to claim 1, wherein the securing device is designed as a guard locking assembly for locking the needle guard in the safe position.

3. The injection device according to claim 1, further comprising an injection connecting assembly for fixing the protective component on the syringe when the needle guard is in the injection position in an interlocking manner.

4. The injection device according to claim 3, wherein the injection connecting assembly is designed as an injection locking assembly for locking the needle guard in the injection position.

5. The injection device according to claim 4, wherein the protective telescoping sleeve comprises a pressure region which is marked on the protective telescoping sleeve; and
   wherein the injection locking assembly is configured to be released when pressure is being exerted on the pressure region.

6. The injection device according to claim 1, wherein the securing device comprises at least one row of locking teeth arranged one in front of the other along at least one of the telescoping sleeves, wherein an opposing locking element of another of the telescoping sleeves, adjacent to the at least one of the telescoping sleeves, of the needle guard engages into said at least one row.

7. The injection device according to claim 1, the needle guard further comprising at least one tongue/groove guide device for ensuring a telescoping guideway and rotation prevention disposed between two of the telescoping sleeves that are adjacent one another.

8. The injection device according to claim 1, where at least one part of the needle guard comprises a multicomponent injection-molded piece.

9. The injection device according to claim 8, wherein the at least one part of the needle guard that comprises a multicomponent injection-molded piece comprises at least first and second injection-molded portions; and
   wherein the first and second injection-molded portions of the multicomponent injection-molded piece are made from two different materials having different hardnesses.

10. The injection device according to claim 1, wherein the interlocking adapter is locked on to the container of the syringe by means of latching hooks.

11. The injection device according to claim 10, wherein the connecting telescoping sleeve is connected axially to the interlocking adapter via a plurality of latching elements which are formed on unattached ends of locking tongues of the interlocking adapter.

* * * * *